US009259549B2

(12) United States Patent
Lang et al.

(10) Patent No.: US 9,259,549 B2
(45) Date of Patent: *Feb. 16, 2016

(54) BREATHING MASK ARRANGEMENT AND A FOREHEAD SUPPORT DEVICE FOR SAME

(71) Applicant: ResMed R&D Germany GmbH, Martinsried (DE)

(72) Inventors: Bernd Christoph Lang, Grafelfing (DE); Achim Biener, Aufkirchen (DE); Dieter Heidmann, Geretsried (DE); Harald Wolfgang Vogele, Gauting (DE); Stefan Rolf Madaus, Krailling (DE)

(73) Assignee: ResMed R&D Germany GmbH, Martinsried (DE)

( * ) Notice: Subject to any disclaimer, the term of this patent is extended or adjusted under 35 U.S.C. 154(b) by 316 days.

This patent is subject to a terminal disclaimer.

(21) Appl. No.: 13/782,102

(22) Filed: Mar. 1, 2013

(65) Prior Publication Data

US 2013/0174850 A1  Jul. 11, 2013

Related U.S. Application Data

(60) Continuation of application No. 12/461,901, filed on Aug. 27, 2009, now Pat. No. 8,402,972, which is a division of application No. 11/128,399, filed on May 13, 2005, now Pat. No. 7,654,263, which is a continuation of application No. 10/221,572, filed as application No. PCT/EP02/02877 on Mar. 14, 2002, now Pat. No. 7,000,614.

(30) Foreign Application Priority Data

Jan. 17, 2002  (DE) .................................. 102 01 682

(51) Int. Cl.
*A61M 11/00* (2006.01)
*A61M 16/06* (2006.01)

(52) U.S. Cl.
CPC ........... *A61M 16/0683* (2013.01); *A61M 16/06* (2013.01); *A61M 16/0638* (2014.02)

(58) Field of Classification Search
CPC ..................... A61M 16/0633; A61M 16/0638; A61M 2210/0618
USPC ............. 128/205.25, 206.11–206.13, 206.16, 128/206.18, 206.21, 206.23, 128/206.24–206.28, 207.11, 207.13
See application file for complete search history.

(56) References Cited

U.S. PATENT DOCUMENTS

| 4,429 A | 3/1846 | Cooke et al. |
| 35,724 A | 6/1862 | Wilcox |

(Continued)

FOREIGN PATENT DOCUMENTS

| AU | 91/77110 B | 11/1991 |
| AU | 94/64816 B | 12/1994 |

(Continued)

OTHER PUBLICATIONS

U.S. Appl. No. 13/923,671, filed Jun. 21, 2013.

(Continued)

*Primary Examiner* — Steven Douglas
(74) *Attorney, Agent, or Firm* — Nixon & Vanderhye P.C.

(57) ABSTRACT

A breathing mask arrangement includes a frame portion, a sealing lip provided to the frame portion and adapted to form a seal with a user's face, a forehead support provided to the frame portion, and a forehead cushion removably secured to the forehead support. The forehead cushion includes a contact portion having a contact surface adapted to contact a user's forehead and a connecting structure structured to couple the forehead cushion to the forehead support and allow pivoting and/or tilting movement of the contact portion relative to the forehead support. The connecting structure includes a support foot adapted to be received within a respective opening provided in the forehead support.

29 Claims, 10 Drawing Sheets

(56) References Cited

U.S. PATENT DOCUMENTS

| | | |
|---|---|---|
| 364,394 A | 6/1887 | Bright |
| 428,592 A | 5/1890 | Chapman |
| 463,351 A | 11/1891 | Elliott |
| 715,611 A | 12/1902 | Schnenker et al. |
| 716,530 A | 12/1902 | Giddens |
| 781,516 A | 1/1905 | Guthrie |
| 812,706 A | 2/1906 | Warbasse |
| 1,070,986 A | 8/1913 | Richter |
| 1,081,745 A | 12/1913 | Johnston et al. |
| 1,176,886 A | 3/1916 | Ermold |
| 1,192,186 A | 7/1916 | Greene |
| 1,206,045 A | 11/1916 | Smith |
| 1,333,075 A | 3/1920 | Hill et al. |
| 1,381,826 A | 6/1921 | Hansen |
| 1,502,450 A | 7/1924 | Wood |
| 1,610,793 A | 12/1926 | Kaufman |
| 1,632,449 A | 6/1927 | McKesson |
| 1,653,572 A | 12/1927 | Jackson |
| 1,672,165 A | 6/1928 | Lewis |
| 1,733,020 A | 10/1929 | Jones |
| 1,837,591 A | 12/1931 | Shindel |
| 1,926,027 A | 9/1933 | Biggs |
| 2,029,129 A | 1/1936 | Schwartz |
| 2,033,448 A | 3/1936 | James |
| 2,123,353 A | 7/1938 | Catt |
| 2,130,555 A | 9/1938 | Malcom |
| 2,133,699 A | 10/1938 | Heidbrink |
| 2,141,222 A | 12/1938 | Pioch |
| 2,149,067 A | 2/1939 | Otero |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,287,353 A | 6/1942 | Minnick |
| 2,317,608 A | 4/1943 | Heidbrink |
| 2,359,506 A | 10/1944 | Battley et al. |
| 2,371,965 A | 3/1945 | Lehmberg |
| 2,376,871 A | 5/1945 | Fink |
| 2,382,364 A | 8/1945 | Yant |
| 2,415,846 A | 2/1947 | Randall |
| 2,428,451 A | 10/1947 | Emerson |
| 2,438,058 A | 3/1948 | Kincheloe |
| 2,454,103 A | 11/1948 | Swidersky |
| 2,473,518 A | 6/1949 | Garrard et al. |
| D156,060 S | 11/1949 | Wade |
| D161,337 S | 12/1950 | Hill |
| 2,540,567 A | 2/1951 | Bennett |
| 2,578,621 A | 12/1951 | Yant |
| 2,590,006 A | 3/1952 | Gordon |
| 2,617,751 A | 11/1952 | Bickett |
| 2,625,155 A | 1/1953 | Engelder |
| 2,638,161 A | 5/1953 | Jones |
| 2,664,084 A | 12/1953 | Hammermann |
| 2,693,178 A | 11/1954 | Gilroy |
| 2,706,983 A | 4/1955 | Matheson et al. |
| 2,747,464 A | 5/1956 | Bowerman |
| 2,820,651 A | 1/1958 | Phillips |
| 2,823,671 A | 2/1958 | Garelick |
| 2,832,015 A | 4/1958 | Ortega |
| 2,837,090 A | 6/1958 | Bloom et al. |
| 2,868,196 A | 1/1959 | Stampe |
| 2,875,757 A | 3/1959 | Galleher, Jr. |
| 2,893,387 A | 7/1959 | Gongoll et al. |
| 2,902,033 A | 9/1959 | Galleher, Jr. |
| 2,917,045 A | 12/1959 | Schildknecht et al. |
| 2,931,355 A | 4/1960 | Schwarz |
| D188,084 S | 5/1960 | Garelick |
| 2,939,458 A | 6/1960 | Lundquist |
| 3,013,556 A | 12/1961 | Galleher |
| 3,042,035 A | 7/1962 | Coanda |
| 3,117,574 A | 1/1964 | Replogle |
| 3,141,213 A | 7/1964 | Nicholas |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,288,138 A | 11/1966 | Sachs |
| 3,315,672 A | 4/1967 | Cunningham et al. |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,474,783 A | 10/1969 | Ulmann |
| 3,494,072 A | 2/1970 | Olson |
| 3,523,534 A | 8/1970 | Nolan |
| 3,535,810 A | 10/1970 | Baehrle |
| 3,555,752 A | 1/1971 | Bogaert |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,725,953 A | 4/1973 | Johnson et al. |
| 3,726,275 A | 4/1973 | Jackson et al. |
| 3,750,333 A | 8/1973 | Vance |
| 3,752,157 A | 8/1973 | Malmin |
| 3,779,164 A | 12/1973 | Study |
| 3,796,216 A | 3/1974 | Schwarz |
| D231,803 S | 6/1974 | Huddy |
| 3,824,999 A | 7/1974 | King |
| 3,830,230 A | 8/1974 | Chester |
| 3,978,854 A | 9/1976 | Mills, Jr. |
| 4,034,426 A | 7/1977 | Hardwick et al. |
| 4,049,357 A | 9/1977 | Hamisch, Jr. |
| 4,062,357 A | 12/1977 | Laerdal |
| 4,064,875 A | 12/1977 | Cramer et al. |
| 4,069,516 A | 1/1978 | Watkins, Jr. |
| 4,077,404 A | 3/1978 | Elam |
| D248,497 S | 7/1978 | Slosek |
| 4,111,197 A | 9/1978 | Warncke et al. |
| D250,131 S | 10/1978 | Lewis et al. |
| 4,120,302 A | 10/1978 | Ziegler |
| 4,121,580 A | 10/1978 | Fabish |
| 4,156,426 A | 5/1979 | Gold |
| 4,161,946 A | 7/1979 | Zuesse |
| 4,164,942 A | 8/1979 | Beard et al. |
| 4,167,185 A | 9/1979 | Lewis |
| 4,201,205 A | 5/1980 | Bartholomew |
| 4,226,234 A | 10/1980 | Gunderson |
| 4,231,363 A | 11/1980 | Grimes |
| 4,233,972 A | 11/1980 | Hauff et al. |
| 4,245,632 A | 1/1981 | Houston |
| 4,248,218 A | 2/1981 | Fischer |
| 4,265,239 A | 5/1981 | Fischer, Jr. et al. |
| 4,266,540 A | 5/1981 | Panzik et al. |
| 4,274,404 A | 6/1981 | Molzan et al. |
| 4,275,908 A | 6/1981 | Elkins et al. |
| D262,322 S | 12/1981 | Mizerak |
| 4,304,229 A | 12/1981 | Curtin |
| 4,328,797 A | 5/1982 | Rollins et al. |
| 4,337,767 A | 7/1982 | Yahata |
| 4,347,205 A | 8/1982 | Stewart |
| 4,354,488 A | 10/1982 | Bartos |
| 4,369,284 A | 1/1983 | Chen |
| 4,380,102 A | 4/1983 | Hansson |
| 4,402,316 A | 9/1983 | Gadberry |
| 4,412,537 A | 11/1983 | Tiger |
| 4,414,973 A | 11/1983 | Matheson et al. |
| 4,417,575 A | 11/1983 | Hilton et al. |
| 4,446,576 A | 5/1984 | Hisataka |
| 4,454,880 A | 6/1984 | Muto et al. |
| 4,454,881 A | 6/1984 | Huber et al. |
| 4,458,679 A | 7/1984 | Ward |
| 4,467,799 A | 8/1984 | Steinberg |
| 4,494,538 A | 1/1985 | Ansite |
| 4,506,665 A | 3/1985 | Andrews et al. |
| 4,522,639 A | 6/1985 | Ansite et al. |
| 4,549,334 A | 10/1985 | Miller |
| 4,558,710 A | 12/1985 | Eichler |
| 4,572,323 A | 2/1986 | Randall |
| 4,579,113 A | 4/1986 | McCreadie et al. |
| 4,580,556 A | 4/1986 | Kondur |
| 4,593,688 A | 6/1986 | Payton |
| 4,606,340 A | 8/1986 | Ansite |
| D285,496 S | 9/1986 | Berman |

(56) References Cited

U.S. PATENT DOCUMENTS

| | | |
|---|---|---|
| 4,616,647 A | 10/1986 | McCreadie |
| 4,622,964 A | 11/1986 | Flynn |
| 4,633,972 A | 1/1987 | DeRocher |
| 4,655,213 A | 4/1987 | Rapoport et al. |
| 4,657,010 A | 4/1987 | Wright |
| 4,665,570 A | 5/1987 | Davis |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,707,863 A | 11/1987 | McNeal |
| 4,713,844 A | 12/1987 | Westgate |
| H397 H | 1/1988 | Stark |
| D293,613 S | 1/1988 | Wingler |
| 4,732,147 A | 3/1988 | Fuller |
| 4,739,755 A | 4/1988 | White et al. |
| 4,770,169 A | 9/1988 | Schmoegner et al. |
| 4,772,760 A | 9/1988 | Graham |
| 4,774,941 A | 10/1988 | Cook |
| 4,782,832 A | 11/1988 | Trimble et al. |
| 4,783,029 A | 11/1988 | Geppert et al. |
| 4,794,921 A | 1/1989 | Lindkvist |
| 4,799,477 A | 1/1989 | Lewis |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,827,924 A | 5/1989 | Japuntich |
| 4,832,017 A | 5/1989 | Schnoor |
| 4,835,820 A | 6/1989 | Robbins, III |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,870,963 A | 10/1989 | Carter |
| 4,875,714 A | 10/1989 | Lee |
| 4,875,718 A | 10/1989 | Marken |
| 4,886,058 A | 12/1989 | Brostrom et al. |
| 4,898,174 A | 2/1990 | Fangrow, Jr. |
| 4,899,614 A | 2/1990 | Kataumi |
| 4,905,683 A | 3/1990 | Cronjaeger |
| 4,905,686 A | 3/1990 | Adams |
| 4,907,584 A | 3/1990 | McGinnis |
| 4,910,806 A | 3/1990 | Baker et al. |
| 4,915,105 A | 4/1990 | Lee |
| 4,915,106 A | 4/1990 | Aulgur et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| 4,946,202 A | 8/1990 | Perricone |
| D310,431 S | 9/1990 | Bellm |
| 4,960,121 A | 10/1990 | Nelson et al. |
| 4,971,051 A | 11/1990 | Toffolon |
| 4,974,586 A | 12/1990 | Wandel et al. |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,997,217 A | 3/1991 | Kunze |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,054,482 A | 10/1991 | Bales |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,136,760 A | 8/1992 | Sano et al. |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,156,146 A | 10/1992 | Corces et al. |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer |
| D334,633 S | 4/1993 | Rudolph |
| 5,199,424 A | 4/1993 | Sullivan et al. |
| D335,322 S | 5/1993 | Jones |
| 5,215,336 A | 6/1993 | Worthing |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,253,641 A | 10/1993 | Choate |
| 5,265,595 A | 11/1993 | Rudolph |
| 5,269,296 A | 12/1993 | Landis |
| 5,279,289 A | 1/1994 | Kirk |
| 5,280,784 A | 1/1994 | Kohler |
| 5,291,880 A | 3/1994 | Almovist et al. |
| 5,301,689 A | 4/1994 | Wennerholm |
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |
| 5,334,646 A | 8/1994 | Chen |
| 5,343,878 A | 9/1994 | Scarberry et al. |
| 5,357,945 A | 10/1994 | Messina |
| 5,357,951 A | 10/1994 | Ratner |
| 5,372,130 A | 12/1994 | Stern et al. |
| 5,388,273 A | 2/1995 | Sydor et al. |
| 5,388,571 A | 2/1995 | Roberts et al. |
| 5,390,373 A | 2/1995 | Flory |
| 5,391,248 A | 2/1995 | Brain |
| 5,398,673 A | 3/1995 | Lambert |
| 5,400,781 A | 3/1995 | Davenport |
| 5,404,871 A | 4/1995 | Goodman et al. |
| 5,411,021 A | 5/1995 | Gdulla et al. |
| 5,419,317 A | 5/1995 | Blasdell et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Soles Bee et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,511,541 A | 4/1996 | Dearstine |
| 5,517,986 A | 5/1996 | Starr et al. |
| 5,522,382 A | 6/1996 | Sullivan et al. |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |

(56) References Cited

U.S. PATENT DOCUMENTS

| | | |
|---|---|---|
| RE35,339 E | 10/1996 | Rapoport |
| 5,560,354 A | 10/1996 | Berthon-Jones et al. |
| 5,570,682 A | 11/1996 | Johnson |
| 5,570,684 A | 11/1996 | Behr |
| 5,570,689 A | 11/1996 | Starr et al. |
| 5,575,278 A | 11/1996 | Bonhomme et al. |
| D377,089 S | 12/1996 | Starr et al. |
| 5,592,937 A | 1/1997 | Freund |
| 5,592,938 A | 1/1997 | Scarberry et al. |
| 5,608,647 A | 3/1997 | Rubsamen et al. |
| 5,617,849 A | 4/1997 | Springett et al. |
| 5,642,730 A | 7/1997 | Baran |
| 5,645,049 A | 7/1997 | Foley et al. |
| 5,645,054 A | 7/1997 | Cotner et al. |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,685,296 A | 11/1997 | Zdrojkowski et al. |
| 5,687,715 A | 11/1997 | Landis et al. |
| 5,704,345 A | 1/1998 | Berthon-Jones |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,740,795 A | 4/1998 | Brydon |
| 5,743,414 A | 4/1998 | Baudino |
| 5,746,201 A | 5/1998 | Kidd |
| 5,794,617 A | 8/1998 | Brunell et al. |
| D398,987 S | 9/1998 | Cotner et al. |
| 5,813,423 A | 9/1998 | Kirchgeorg |
| 5,832,918 A | 11/1998 | Pantino |
| 5,839,436 A | 11/1998 | Fangrow et al. |
| D402,755 S | 12/1998 | Kwok |
| 5,860,677 A | 1/1999 | Martins et al. |
| RE36,165 E | 3/1999 | Behr |
| 5,884,624 A | 3/1999 | Barnett et al. |
| 5,896,857 A | 4/1999 | Hely et al. |
| 5,906,199 A | 5/1999 | Budzinski |
| 5,909,732 A | 6/1999 | Diesel et al. |
| 5,921,239 A | 7/1999 | McCall et al. |
| 5,935,136 A | 8/1999 | Hulse et al. |
| 5,937,851 A | 8/1999 | Serowski et al. |
| 5,966,745 A | 10/1999 | Schwartz et al. |
| 5,975,079 A | 11/1999 | Hellings et al. |
| 5,979,025 A | 11/1999 | Horng |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,029,660 A | 2/2000 | Calluaud et al. |
| 6,029,665 A | 2/2000 | Berthon-Jones |
| 6,029,668 A | 2/2000 | Freed |
| 6,039,044 A | 3/2000 | Sullivan |
| D423,096 S | 4/2000 | Kwok |
| 6,044,844 A | 4/2000 | Kwok et al. |
| 6,062,148 A | 5/2000 | Hodge et al. |
| 6,062,221 A | 5/2000 | Brostrom et al. |
| 6,082,360 A | 7/2000 | Rudolph et al. |
| 6,091,973 A | 7/2000 | Colla et al. |
| D428,987 S | 8/2000 | Kwok |
| 6,098,205 A | 8/2000 | Schwartz et al. |
| 6,112,746 A | 9/2000 | Kwok et al. |
| 6,119,693 A | 9/2000 | Kwok et al. |
| 6,123,071 A | 9/2000 | Berthon-Jones et al. |
| 6,152,137 A | 11/2000 | Schwartz et al. |
| 6,189,532 B1 | 2/2001 | Hely et al. |
| 6,192,886 B1 | 2/2001 | Rudolph |
| D439,326 S | 3/2001 | Hecker et al. |
| 6,196,223 B1 | 3/2001 | Belfer et al. |
| D443,355 S | 6/2001 | Gunaratnam et al. |
| 6,240,605 B1 | 6/2001 | Stevens et al. |
| 6,250,375 B1 | 6/2001 | Lee et al. |
| 6,256,846 B1 | 7/2001 | Lee |
| 6,257,237 B1 | 7/2001 | Suzuki |
| 6,272,722 B1 | 8/2001 | Lai |
| 6,321,421 B1 | 11/2001 | Lim |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,374,826 B1 | 4/2002 | Gunaratnam et al. |
| 6,381,813 B1 | 5/2002 | Lai |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,418,928 B1 | 7/2002 | Bordewick et al. |
| 6,422,238 B1 | 7/2002 | Lithgow |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,230 B1 | 8/2002 | Gunaratnam et al. |
| 6,449,817 B1 | 9/2002 | Hsu |
| 6,463,931 B1 | 10/2002 | Kwok et al. |
| 6,467,483 B1 | 10/2002 | Kopacko et al. |
| 6,491,034 B1 | 12/2002 | Gunaratnam |
| 6,494,207 B1 | 12/2002 | Kwok |
| D468,823 S | 1/2003 | Smart |
| 6,513,206 B1 | 2/2003 | Banitt et al. |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok |
| 6,561,190 B1 | 5/2003 | Kwok |
| 6,561,191 B1 | 5/2003 | Kwok |
| 6,581,601 B2 | 6/2003 | Ziaee |
| 6,595,214 B1 | 7/2003 | Hecker |
| 6,615,830 B1 | 9/2003 | Serowski et al. |
| 6,615,832 B1 | 9/2003 | Chen |
| 6,615,834 B2 | 9/2003 | Gradon et al. |
| 6,626,177 B1 | 9/2003 | Ziaee |
| 6,631,718 B1 | 10/2003 | Lovell |
| D484,237 S | 12/2003 | Lang et al. |
| 6,679,260 B2 | 1/2004 | Her |
| 6,679,261 B2 | 1/2004 | Lithgow et al. |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,927 B2 | 3/2004 | Kwok et al. |
| 6,705,647 B1 | 3/2004 | Palmer |
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,789,543 B2 | 9/2004 | Cannon |
| 6,796,308 B2 | 9/2004 | Gunaratnam et al. |
| 6,805,117 B1 | 10/2004 | Ho et al. |
| 6,823,869 B2 | 11/2004 | Raje et al. |
| 6,832,615 B2 | 12/2004 | Hensel |
| D502,260 S | 2/2005 | Lang et al. |
| 6,851,425 B2 | 2/2005 | Jaffre |
| 6,851,428 B2 | 2/2005 | Dennis |
| 6,907,882 B2 | 6/2005 | Ging |
| 6,918,390 B2 | 7/2005 | Lithgow et al. |
| 6,926,004 B2 | 8/2005 | Schumacher |
| 6,968,844 B2 | 11/2005 | Liland et al. |
| 6,973,929 B2 | 12/2005 | Gunaratnam |
| 6,986,352 B2 | 1/2006 | Frater et al. |
| D515,698 S | 2/2006 | Lang et al. |
| 6,997,188 B2 | 2/2006 | Kwok et al. |
| 7,000,614 B2 | 2/2006 | Lang et al. |
| 7,005,414 B2 | 2/2006 | Barnikol et al. |
| 7,007,696 B2 | 3/2006 | Palkon et al. |

(56) References Cited

U.S. PATENT DOCUMENTS

| | | |
|---|---|---|
| 7,011,090 B2 | 3/2006 | Drew et al. |
| 7,021,311 B2 | 4/2006 | Gunaratnam et al. |
| 7,036,508 B2 | 5/2006 | Kwok |
| 7,047,965 B1 | 5/2006 | Ball |
| 7,047,972 B2 | 5/2006 | Ging et al. |
| 7,059,326 B2 | 6/2006 | Heidmann et al. |
| 7,066,179 B2 | 6/2006 | Eaton et al. |
| 7,089,939 B2 | 8/2006 | Walker et al. |
| 7,095,938 B2 | 8/2006 | Tolstikhin |
| 7,100,610 B2 | 9/2006 | Biener et al. |
| 7,107,989 B2 | 9/2006 | Frater et al. |
| 7,112,179 B2 | 9/2006 | Bonutti et al. |
| 7,178,525 B2 | 2/2007 | Matula, Jr. et al. |
| 7,185,652 B2 | 3/2007 | Gunaratnam et al. |
| 7,207,334 B2 | 4/2007 | Smart |
| 7,207,335 B2 | 4/2007 | Kwok et al. |
| 7,216,647 B2 | 5/2007 | Lang et al. |
| 7,219,670 B2 | 5/2007 | Jones et al. |
| 7,234,466 B2 | 6/2007 | Kwok et al. |
| 7,234,773 B2 | 6/2007 | Raftery et al. |
| 7,290,546 B2 | 11/2007 | Sprinkle et al. |
| 7,296,574 B2 | 11/2007 | Ho et al. |
| 7,318,437 B2 | 1/2008 | Gunaratnam et al. |
| 7,318,439 B2 | 1/2008 | Raje et al. |
| 7,320,323 B2 | 1/2008 | Lang et al. |
| 7,353,826 B2 | 4/2008 | Sleeper et al. |
| 7,353,827 B2 | 4/2008 | Geist |
| 7,406,965 B2 | 8/2008 | Kwok et al. |
| 7,461,656 B2 | 12/2008 | Gunaratnam et al. |
| 7,472,704 B2 | 1/2009 | Gunaratnam |
| 7,487,772 B2 | 2/2009 | Ging et al. |
| 7,487,777 B2 | 2/2009 | Gunaratnam et al. |
| 7,503,327 B2 | 3/2009 | Gunaratnam |
| 7,509,958 B2 | 3/2009 | Amarasinghe et al. |
| 7,523,754 B2 | 4/2009 | Lithgow et al. |
| 7,610,916 B2 | 11/2009 | Kwok et al. |
| 7,614,400 B2 | 11/2009 | Lithgow et al. |
| 7,621,274 B2 | 11/2009 | Sprinkle et al. |
| 7,654,263 B2 | 2/2010 | Lang et al. |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,814,911 B2 | 10/2010 | Bordewick et al. |
| 7,819,119 B2 | 10/2010 | Ho |
| 7,827,987 B2 | 11/2010 | Woodard et al. |
| 7,827,990 B1 | 11/2010 | Melidis et al. |
| 7,841,345 B2 | 11/2010 | Guney et al. |
| 7,856,698 B2 | 12/2010 | Hays |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,882,837 B2 | 2/2011 | Kwok et al. |
| 7,900,635 B2 | 3/2011 | Gunaratnam et al. |
| 7,942,148 B2 | 5/2011 | Davidson et al. |
| 7,942,149 B2 | 5/2011 | Gunaratnam |
| 7,967,013 B2 | 6/2011 | Ging et al. |
| 7,967,014 B2 | 6/2011 | Heidmann et al. |
| 7,992,559 B2 | 8/2011 | Lang et al. |
| 8,042,538 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,113,203 B2 | 2/2012 | Lithgow et al. |
| 8,136,524 B2 | 3/2012 | Ging et al. |
| 8,186,348 B2 | 5/2012 | Kwok et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,230,855 B2 | 7/2012 | Raje et al. |
| 2003/0019496 A1 | 1/2003 | Kopacko et al. |
| 2003/0034034 A1 | 2/2003 | Kwok et al. |
| 2003/0062048 A1 | 4/2003 | Gradon |
| 2003/0075180 A1 | 4/2003 | Raje et al. |
| 2003/0075182 A1 | 4/2003 | Heidmann et al. |
| 2003/0084904 A1 | 5/2003 | Gunaratnam |
| 2003/0089373 A1 | 5/2003 | Gradon |
| 2003/0115662 A1 | 6/2003 | Dobbie et al. |
| 2003/0196656 A1 | 10/2003 | Moore et al. |
| 2003/0221691 A1 | 12/2003 | Biener et al. |
| 2004/0045550 A1 | 3/2004 | Lang et al. |
| 2004/0045551 A1 | 3/2004 | Eaton |
| 2004/0094157 A1 | 5/2004 | Dantanarayana et al. |
| 2004/0112385 A1 | 6/2004 | Drew |
| 2004/0112387 A1 | 6/2004 | Lang et al. |
| 2004/0118406 A1 | 6/2004 | Lithgow et al. |
| 2004/0177850 A1 | 9/2004 | Gradon |
| 2004/0211428 A1 | 10/2004 | Jones, Jr. et al. |
| 2004/0216747 A1 | 11/2004 | Jones et al. |
| 2004/0226566 A1 | 11/2004 | Gunaratnam et al. |
| 2004/0255949 A1 | 12/2004 | Lang et al. |
| 2005/0098183 A1 | 5/2005 | Nash et al. |
| 2005/0199239 A1 | 9/2005 | Lang et al. |
| 2005/0211252 A1 | 9/2005 | Lang et al. |
| 2006/0081250 A1 | 4/2006 | Bordewick et al. |
| 2006/0118117 A1 | 6/2006 | Berthon-Jones et al. |
| 2006/0169286 A1 | 8/2006 | Eifler et al. |
| 2006/0191538 A1 | 8/2006 | Heidmann et al. |
| 2006/0219246 A1 | 10/2006 | Dennis |
| 2006/0254593 A1 | 11/2006 | Chang |
| 2006/0283461 A1 | 12/2006 | Lubke et al. |
| 2007/0044804 A1 | 3/2007 | Matula et al. |
| 2007/0137653 A1 | 6/2007 | Wood |
| 2007/0144525 A1 | 6/2007 | Davidson et al. |
| 2008/0178885 A1 | 7/2008 | Raje et al. |
| 2008/0257354 A1 | 10/2008 | Davidson et al. |
| 2008/0264421 A1 | 10/2008 | Kwok et al. |
| 2008/0314389 A1 | 12/2008 | Thomas et al. |
| 2009/0044808 A1 | 2/2009 | Guney |
| 2009/0050156 A1 | 2/2009 | Ng et al. |
| 2009/0126739 A1 | 5/2009 | Ng et al. |
| 2009/0139526 A1 | 6/2009 | Melidis et al. |
| 2009/0173343 A1 | 7/2009 | Omura et al. |
| 2009/0223521 A1 | 9/2009 | Howard et al. |
| 2010/0000543 A1 | 1/2010 | Berthon-Jones et al. |
| 2010/0071700 A2 | 3/2010 | Hitchcock et al. |
| 2010/0089401 A1 | 4/2010 | Lang et al. |
| 2010/0282265 A1 | 11/2010 | Melidis et al. |
| 2010/0300447 A1 | 12/2010 | Biener et al. |
| 2011/0030692 A1 | 2/2011 | Jones et al. |
| 2011/0056498 A1 | 3/2011 | Lang et al. |
| 2011/0094516 A1 | 4/2011 | Chang |
| 2011/0174311 A1 | 7/2011 | Gunaratnam |
| 2011/0220111 A1 | 9/2011 | Heidmann et al. |
| 2011/0226254 A1 | 9/2011 | Lang et al. |
| 2011/0259337 A1 | 10/2011 | Hitchcock et al. |
| 2012/0174928 A1 | 7/2012 | Raje et al. |
| 2013/0199536 A1 | 8/2013 | Biener et al. |

FOREIGN PATENT DOCUMENTS

| | | |
|---|---|---|
| AU | 95/16178 B | 7/1995 |
| AU | 32914/95 | 2/1996 |
| AU | 9459430 | 2/1996 |
| AU | A 41018/97 | 4/1998 |
| AU | A 89312/98 | 1/1999 |
| AU | 200071882 | 6/2001 |
| CA | 1039144 | 9/1928 |
| CA | 618807 | 4/1961 |
| CA | 623129 | 7/1961 |
| CA | 88122 | 11/1999 |
| CN | 1326371 | 12/2001 |
| CN | 2464353 | 12/2001 |
| CN | 1408453 | 4/2003 |
| DE | 284 800 C | 11/1913 |
| DE | 459 104 | 4/1928 |
| DE | 701 690 | 1/1941 |
| DE | 923 500 | 2/1955 |
| DE | 159396 | 6/1981 |
| DE | 3015279 A1 | 10/1981 |
| DE | 3345067 A1 | 6/1984 |
| DE | 37 07 952 | 3/1987 |

(56) References Cited

FOREIGN PATENT DOCUMENTS

| | | |
|---|---|---|
| DE | 3537507 | 4/1987 |
| DE | 3539073 A1 | 5/1987 |
| DE | 4004157 C1 | 4/1991 |
| DE | 42 12 259 | 1/1993 |
| DE | 42 33 448 | 4/1993 |
| DE | 4343205 A1 | 6/1995 |
| DE | 195 48 380 | 7/1996 |
| DE | 196 03 949 | 8/1997 |
| DE | 29715718 | 10/1997 |
| DE | 197 35 359 | 1/1998 |
| DE | 297 21 766 | 3/1998 |
| DE | 297 23 101 U1 | 7/1998 |
| DE | 298 10846 U1 | 8/1998 |
| DE | 198 17 332 A1 | 1/1999 |
| DE | 49900269.5 | 1/1999 |
| DE | 198 07 961 | 8/1999 |
| DE | 198 01 105 A1 | 9/1999 |
| DE | 299 23 126 | 3/2000 |
| DE | 299 23 141 | 3/2000 |
| DE | 20005346 | 5/2000 |
| DE | 29923141 U | 5/2000 |
| DE | 200 17 940 | 2/2001 |
| DE | 199 54 57 A1 | 6/2001 |
| DE | 199 62 515 | 7/2001 |
| DE | 100 51 891 | 5/2002 |
| DE | 10045183 | 5/2002 |
| DE | 198 40 760 | 3/2003 |
| DE | 103 31 837 | 1/2005 |
| DE | 103 38 169 | 3/2005 |
| EP | 0 054 154 | 10/1981 |
| EP | 0 252 052 A1 | 1/1988 |
| EP | 0 264 772 A1 | 4/1988 |
| EP | 0 334 555 | 9/1989 |
| EP | 0 386 605 A1 | 2/1990 |
| EP | 0427474 A2 | 5/1991 |
| EP | 0 462 701 A1 | 12/1991 |
| EP | 0 303 090 B1 | 4/1992 |
| EP | 0 549 299 | 6/1993 |
| EP | 0 602 424 | 11/1993 |
| EP | 0 608 684 A1 | 8/1994 |
| EP | 0 0697 225 | 7/1995 |
| EP | 178 925 A2 | 4/1996 |
| EP | 0 747 078 A2 | 12/1996 |
| EP | 0 821 978 | 2/1998 |
| EP | 0 853 962 | 7/1998 |
| EP | 0 911 050 | 4/1999 |
| EP | 0 958 841 | 11/1999 |
| EP | 1027905 A2 | 8/2000 |
| EP | 1 057 494 | 12/2000 |
| EP | 1057494 A2 | 12/2000 |
| EP | 1099452 | 5/2001 |
| EP | 1205205 | 11/2001 |
| EP | 1 163 923 | 12/2001 |
| EP | 1 334 742 | 8/2003 |
| EP | 1 356 843 | 10/2003 |
| EP | 1 555 039 | 7/2005 |
| ES | 145309 | 1/2000 |
| FR | 780018 | 4/1935 |
| FR | 2 574 657 A1 | 6/1986 |
| FR | 2 658 725 A1 | 8/1991 |
| FR | 2 691 906 | 12/1993 |
| FR | 2 720 280 | 12/1995 |
| FR | 2 749 176 | 2/1997 |
| FR | 99/16 | 8/1999 |
| GB | 649 689 | 1/1951 |
| GB | 823 887 | 11/1959 |
| GB | 1395391 | 5/1975 |
| GB | 1 467 628 | 3/1977 |
| GB | 2145335 A | 3/1985 |
| GB | 2147506 A | 5/1985 |
| GB | 2 164 569 A | 3/1986 |
| GB | 2 186 801 | 8/1987 |
| GB | 2 257 648 A | 12/1993 |
| GB | 2080119 | 12/1998 |
| GB | 2080120 | 12/1998 |
| GB | 2080121 | 12/1998 |
| JP | S39-13991 | 7/1964 |
| JP | S48-55696 | 10/1971 |
| JP | S52-76695 | 6/1977 |
| JP | S52-164619 | 12/1977 |
| JP | S59-55535 | 4/1984 |
| JP | S61-67747 | 5/1986 |
| JP | H07-21058 | 4/1995 |
| JP | H07-308381 | 11/1995 |
| JP | H09-501084 | 2/1997 |
| JP | 09/216240 A | 8/1997 |
| JP | H09-292588 | 11/1997 |
| JP | 11-000397 | 1/1999 |
| JP | 1105649 | 2/1999 |
| JP | H11-104256 | 4/1999 |
| JP | H11-508159 | 7/1999 |
| JP | H11-381522 | 11/1999 |
| JP | 2000-135103 | 5/2000 |
| JP | 2000-225191 | 8/2000 |
| JP | 2000-279520 | 10/2000 |
| JP | 2000-325481 | 11/2000 |
| JP | 2000-515784 | 11/2000 |
| JP | 2002-028240 | 1/2002 |
| JP | 2002-543943 | 12/2002 |
| JP | 2003-502119 | 2/2003 |
| JP | 2003-175106 | 6/2003 |
| JP | 2003-190308 | 7/2003 |
| JP | 2004-329941 | 11/2004 |
| JP | 2005-506156 | 3/2005 |
| JP | 3686609 | 8/2005 |
| SE | 65 481 | 8/2000 |
| WO | WO 80/01044 | 5/1980 |
| WO | WO 80/01645 | 8/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 95/04566 | 2/1995 |
| WO | WO 96/17643 | 6/1996 |
| WO | WO 96/25983 | 8/1996 |
| WO | WO 96/39206 | 12/1996 |
| WO | WO 97/00092 | 1/1997 |
| WO | WO 97/07847 | 3/1997 |
| WO | WO 97/09090 | 3/1997 |
| WO | WO 97/41911 | 11/1997 |
| WO | WO 98/04310 | 2/1998 |
| WO | WO 98/11930 | 3/1998 |
| WO | WO 9812965 | 4/1998 |
| WO | WO 98/18514 | 5/1998 |
| WO | WO 98/24499 | 6/1998 |
| WO | WO 98/26330 | 6/1998 |
| WO | WO 98/26629 | 6/1998 |
| WO | WO 98/30123 | 7/1998 |
| WO | WO 9834665 | 8/1998 |
| WO | WO 98/48878 | 11/1998 |
| WO | WO 99/58181 | 1/1999 |
| WO | WO 99/21618 | 5/1999 |
| WO | WO 99/30760 | 6/1999 |
| WO | WO 9943373 | 9/1999 |
| WO | WO 99/61088 | 12/1999 |
| WO | WO 99/65554 | 12/1999 |
| WO | WO 00/78384 | 2/2000 |
| WO | WO 00/21600 | 4/2000 |
| WO | WO 00/35525 | 6/2000 |
| WO | WO 00/38772 | 7/2000 |
| WO | WO 00/50121 | 8/2000 |
| WO | WO 00/57942 | 10/2000 |
| WO | WO 00/69521 | 11/2000 |
| WO | WO 0078381 | 12/2000 |
| WO | WO 01/62326 | 8/2001 |
| WO | WO 01/97892 | 12/2001 |

(56) References Cited

FOREIGN PATENT DOCUMENTS

| WO | WO 01/97893 | 12/2001 |
|----|----|----|
| WO | WO 02/07806 | 1/2002 |
| WO | WO 02/11804 | 2/2002 |
| WO | WO 02/32491 | 4/2002 |
| WO | WO 02/45784 | 6/2002 |
| WO | WO 02/47749 | 6/2002 |
| WO | WO 03/005931 | 1/2003 |
| WO | WO 03/035156 | 5/2003 |
| WO | WO 03/059427 | 7/2003 |
| WO | WO 03/082406 | 10/2003 |
| WO | WO 03/105921 | 12/2003 |
| WO | WO 2004/012803 | 2/2004 |
| WO | WO 2004/021960 | 3/2004 |
| WO | WO 2004/022145 | 3/2004 |
| WO | WO 2004/022146 | 3/2004 |
| WO | WO 2004/022147 | 3/2004 |
| WO | WO 2004022144 | 3/2004 |
| WO | WO 2004022145 | 3/2004 |
| WO | WO 2004/041342 | 5/2004 |
| WO | WO 2004/073778 | 9/2004 |
| WO | WO/2004/078228 | 9/2004 |
| WO | WO 2004/096332 | 11/2004 |
| WO | WO 2005/002656 | 1/2005 |
| WO | WO 2005/018523 | 3/2005 |
| WO | WO 2005/028010 | 3/2005 |
| WO | WO 2005/063326 | 7/2005 |
| WO | WO 2005/063328 | 7/2005 |
| WO | WO 2005/068002 | 7/2005 |
| WO | WO 2005/094928 | 10/2005 |
| WO | WO 2005/123166 | 12/2005 |
| WO | WO 2006/000046 | 1/2006 |
| WO | WO 2006/074513 | 7/2006 |
| WO | WO 2006/074515 | 7/2006 |
| WO | WO 2006/074516 | 7/2006 |
| WO | WO 2006/138416 | 12/2006 |
| WO | WO 2007/045008 | 4/2007 |
| WO | WO 2007/048174 | 5/2007 |
| WO | WO 2009/026627 | 3/2009 |
| WO | WO 2009/052560 | 4/2009 |
| WO | WO 2009/062265 | 5/2009 |
| WO | WO 2009/108995 | 9/2009 |
| WO | WO 2010/066004 | 6/2010 |

OTHER PUBLICATIONS 4 additional photographs of "Weinmann Mask," before applicants' filing date.
Australian Appln. No. 2005253641—Examiner's First Report, dated Apr. 20, 2010.
Australian Appln. No. 2005253641—Examiner's Report, dated Aug. 18, 2011.
Australian Appln. No. 2005256167—Examiner's First Report, dated Apr. 29, 2010.
Australian Appln. No. 2006206044—Examiner's First Report, dated Dec. 1, 2010.
Australian Appln. No. 2010201443—Examiner's First Report, dated Jun. 22, 2011.
Australian Appln. No. 2010251884—Examination Report, dated Jul. 27, 2012.
Chinese Appln. No. 200410038106.7—Office Action (w/English translation), dated Jun. 15, 2007.
Chinese Appln. No. 200480011911.9—Office Action (w/English translation), dated Jun. 24, 2010.
Chinese Appln. No. 200480040220.1—Office Action English translation, before applicants' filing date.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200580021230.5—Office Action (w/English translation), dated Jul. 3, 2009.
Chinese Appln. No. 200910223650.1—Office Action (w/English translation), dated Mar. 29, 2012.
Chinese Appln. No. 201010508994.X—Office Action (w/ English translation), dated Jun. 15, 2011.
Chinese Appln. No. 201010517066.X—Office Action (w/English translation), dated Nov. 10, 2011.
Chinese Appln. No. 201010620187.7—Office Action (w/English translation), dated Oct. 26, 2011.
Chinese Appln. No. 201010620187.7—Office Action (w/English translation), dated Jul. 10, 2012.
DeVilbiss Serenity Mask—Instruction Guide 9352 Series, before applicants' filing date.
DeVilbiss Serenity Mask—Mask Accessories, before applicants' filing date.
European Appln. No. EP 02445110.6—Search Report, dated Nov. 6, 2003.
European Appln. No. EP 02714190.2—Search Report, dated Jul. 11, 2006.
European Appln. No. EP 03793491.6—Supplementary Search Report, dated Jun. 15, 2010.
European Appln. No. EP 04802114.1—Supplementary Search Report, dated Apr. 27, 2009.
European Appln. No. EP 05749447.8—Supplementary Search Report, dated Dec. 2, 2009.
European Appln. No. EP 05753870.4—Supplementary Search Report, dated Dec. 15, 2009.
European Appln. No. EP 05753870.4—Office Action, dated Jul. 19, 2010.
European Appln. No. EP 06704773.8—Supplementary Search Report, dated Mar. 29, 2011.
European Appln. No. EP 08161868.8—Search Report, dated Sep. 23, 2008.
European Appln .No. EP 09003544.5—Search Report, dated Jun. 2, 2009.
European Appln. No. EP 10166255.9—Search Report, dated Oct. 25, 2010.
European Appln. No. EP 10181516.5—Search Report, dated Jun. 13, 2012.
European Appln. No. EP 10182015.7—Search Report, dated Jun. 15, 2012.
European Appln. No. EP 10185071.7—Search Report, dated Dec. 6, 2010.
European Appln. No. EP 10185072.5—Search Report, dated Dec. 6, 2010.
European Appln. No. EP 10185073.3—Search Report, dated Dec. 6, 2010.
European Appln. No. EP 12165749.8—Extended Search Report, dated Oct. 10, 2012.
European Appln. No. EP 12165751.4—Extended Search Report, dated Oct. 8, 2012.
Japanese Appln. No. S52-164619—English translation of Figure 1, Dec. 1977.
Japanese Appln. No. 2000-029094—Office Action (w/English translation), before applicants' filing date.
Japanese Appln. No. 2001-504444—Office Action (w/English translation), dated Oct. 26, 2004.
Japanese Appln. No. 2003-559587—Office Action (w/English translation), dated Mar. 17, 2009.
Japanese Appln. No. 2004-137431—Office Action (w/English translation), dated Dec. 8, 2009.
Japanese Appln. No. 2004-569777—Office Action (w/English translation), dated Mar. 3, 2009.
Japanese Appln. No. 2005-004072—Office Action (w/English translation), dated Sep. 24, 2009.
Japanese Appln. No. 2006-504029—Office A545843ction (w/English translation), dated Nov. 10, 2009.
Japanese Appln. No. 2006-545843—Notice of Reasons for Rejection (w/English translation), dated Jun. 7, 2011.
Japanese Appln. No. 2007-515732—Office Action (w/English translation), dated Aug. 24, 2010.

(56) References Cited

OTHER PUBLICATIONS

Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-516895—Office Action (w/English translation), dated Aug. 24, 2010.
Japanese Appln. No. 2007-550640—Office Action (w/English translation), dated Mar. 29, 2011.
Japanese Appln. No. 2007-550640—Office Action (w/English translation), dated Mar. 27, 2012.
Japanese Appln. No. 2008-318985—Office Action (w/English translation), dated Jun. 14, 2011.
Japanese Appln. No. 2010-268127—Notice of Reasons for Rejection (w/English translation), dated Jul. 10, 2012.
Japanese Appln. No. 2011-038110—Office Action (w/English translation), dated Aug. 14, 2012.
New Zealand Appln. No. 556041—Examination Report, dated May 6, 2011.
New Zealand Appln. No. 564877—Examination Report, dated Dec. 2, 2009.
New Zealand Appln. No. 567375—Examination Report, dated Nov. 17, 2009.
New Zealand Appln. No. 587820—Examination Report, dated Sep. 13, 2010.
New Zealand Appln. No. 592219—Examination Report, dated Apr. 11, 2011.
New Zealand Appln. No. 597689—Examination Report, dated Jan. 25, 2012.
PCT/AU03/01160—International Search Report, dated Oct. 8, 2003.
PCT/AU2004/001760—International Search Report, dated Jan. 12, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2005/000850—International Search Report, dated Aug. 12, 2005.
PCT/AU2005/000850—International Preliminary Report on Patentability, dated Dec. 20, 2006.
PCT/AU2005/000931—International Search Report, dated Jul. 19, 2005.
PCT/AU2005/000931—International Preliminary Report on Patentability, dated Dec. 28, 2006.
PCT/AU2006/000037—International Search Report, dated Mar. 17, 2006.
PCT/AU2006/001570—International Search Report, dated Jan. 5, 2007.
PCT/AU2009/000241—International Search Report, dated May 18, 2009.
PCT/AU2009/001102—International Search Report, dated Dec. 11, 2009.
PCT/AU2010/000657—International Search Report, dated Sep. 9, 2010.
PCT/EP2004/012811—International Search Report, dated Apr. 12, 2005.
ResCare Limited, "Sullivan™ Nasal CPAP System, Nose Mask Clip—User Instructions" 5/90, 1 page, before applicants' filing date.
ResMed Ltd., "Improving patient compliance with the ResMed Range of Mask Systems the Ultimate Interface for CPAP treatment," before applicants' filing date, 4 pages.
ResMed, Mask Systems Product Brochure, Sep. 1992, 2 pages.
Respironics, Inc., "Nasal Mask System Silicone Contour Mask," Product Instructions, Jun. 1997, 2 pages.
U.S. Appl. No. 12/083,779—Office Action, dated Feb. 17, 2012.
U.S. Appl. No. 12/083,779—Office Action, dated Sep. 28, 2012.
U.S. Appl. No. 60/227,472, filed Aug. 2000 (expired).
U.S. Appl. No. 60/424,696, filed Nov. 8, 2002 (expired).
U.S. Appl. No. 60/467,572, filed May 2003 (expired).
U.S. Appl. No. 60/643,121, filed Jan. 12, 2005 (expired).
Office Action dated Oct. 7, 2008, filed in Japanese Appln. No. 2003-537718 (English translation); 11 pages.
Decision Dated Dec. 6, 2007 (Received on Feb. 4, 2008); Opposition hearing by Weinmann . . . against German Patent 101 51 984 (including English Translation of the Decision).
Various invoices relating to the "Somnomask," as well as a brochure of the model "Somnomask" of 1999.
U.S. Appl. No. 11/987,164, filed Nov. 28, 2007.
U.S. Appl. No. 11/491,964, filed Jul. 25, 2006.
U.S. Appl. No. 10/555,301, filed Feb. 1, 2006.
Supplementary Search Report EP Appln. No. 04730413, mailed Sep. 29, 2009, 3 pages.
International Search Report of PCT/AU2004/000563, mailed Jun. 23, 2004.
Search Report issued in EP Application No. 09178736.6, Apr. 19, 2010.
Mask 1 Photographs, Respironics Inc., Reusable Full Mask (small) Part #452033 Lot #951108.
Mask 2 Photographs, Puritan—Bennett Adam Curcuit, Shell Part #231700, Swivel Part #616329-00, Pillows (medium) Part #615324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port. Part #672004, Monarch Headgear, Part #572011.
Mask 5 Photographs. Healthdyne Technologies, Nasal CPAP Mask (medium narrow), Part #702510.
Mask 6 Photographs, Healthdyne Technologies, Soft Series Nasal CPAP Mask. Part #702020.
Mask 7 Photographs DeVilbiss Healthcare Inc., Small Mask and Seal Rings, Part #73510-668.
Mask 6 Photographs, Respironics Inc., Reusable Contour Mask (medium), Part #302180.
Mask 9 Photographs, Healthdyne Technologies, Healtndyne Large Headgear.
Mask 10 Photographs, Respironics Inc., Soft Cap (medium), Part #302142.
Mask 11 Photographs, Weinmann: Hamburg, Nasalmaskensystem mit Schalidämpfer (medium), Part #WN 23105.
Mask 12 Photographs, Life Care.
Mask 13 Photographs. Healthdyne Technologies.
Mask 14 Photographs. King System.
Mask 15 Photographs. Respironics Inc., Pediatric Mask.
Mask 16 Photographs. Hans Rudolph Inc. Hans Rudolph Silicone Rubber Face Mask/8900.
Photograph of Weinmann Mask. acquired prior to 1998.
Somotron CPAP-Gerat WM 2300 Instruction Manual, Weinmann Hamburg, 11 pages, 1991.
9 photographs of Weinmann mask. WM 23122, 1991.
The ResMed Range of Mask Systems, product brochure, Nov. 1995, 4 pages.
Product Brochure for ResMed "Sullivan® Mirage™—The Mirage is Real. A Perfect Fit—First Time," © 1997 ResMed Limited, 4 pages.
Product Brochure for ResMed "Sullivan® Mirage™—The Mirage is Real. A Perfect Fit—First Time," © 1998 ResMed Limited, 4 pages.

BREATHING MASK ARRANGEMENT AND A FOREHEAD SUPPORT DEVICE FOR SAME

CROSS-REFERENCE TO RELATED APPLICATIONS

This application is a continuation of U.S. patent application Ser. No. 12/461,901, filed Aug. 27, 2009, allowed, which is a divisional of U.S. application Ser. No. 11/128,399, filed May 13, 2005, now U.S. Pat. No. 7,654,263, which is a continuation of U.S. application Ser. No. 10/221,572, filed Jan. 28, 2003, now U.S. Pat. No. 7,000,614, which is the National Phase of International Application PCT/EP02/02877, filed Mar. 14, 2002, which designated the U.S. and that International Application was not published under PCT Article 21(2) in English, which claims priority to German Application No. 10201682.8, filed Jan. 17, 2002, each of which is incorporated herein by reference in its entirety.

FIELD OF THE INVENTION

The invention concerns a breathing mask arrangement as can be used for example in the context of CPAP-therapy for treating sleep-related respiratory disturbances. The invention further concerns a forehead support device for a breathing mask arrangement.

BACKGROUND OF THE INVENTION

In the context of what is referred to as CPAP-therapy a patient can be supplied by way of a breathing mask arrangement with a breathable gas; in particular ambient air at a pressure level which is above the ambient pressure level. The respiratory gas which is under pressure makes is it possible to provide for pneumatic splinting of the upper respiratory tracts and thus to obviate any obstructions. In the course of implementing pressure respiration or CPAP-therapy the breathing mask arrangements which are required to supply the respiratory gas are usually worn by the patient over the entire sleep or rest phase of the patient. The breathing mask arrangement is usually supported by way of a sealing Up zone in the region around the nose of the person using the mask and by way of a forehead support device in the forehead region of the mask user. The holding forces required to apply the breathing mask arrangement can be afforded by a fixing device which for example has a headband which is passed around the back of the head of the mask user. Under some circumstances, in the region in which the sealing lip device is applied and in the contact region of the forehead support device, surface pressures can occur, which result in the level of comfort involved, in wearing the breathing mask arrangement being seriously adversely affected. In dependence on the individual architecture of the face of the person wearing the mask, considerable mask-pressing forces are m part required in order to achieve the desired sealing integrity, in that situation, in the region of the zones where the breathing mask bears against the face of the patient, unacceptably clearly visible pressure points may also be caused in the forehead region.

OBJECT OF THE INVENTION

The object of the invention is to provide a breathing mask arrangement which can be reliably fixed in a correct application position and which is additionally distinguished by a high level of wearing comfort. Attainment of the object in accordance with the invention In accordance with the invention that, object is attained by a breathing mask arrangement comprising an arch body, a sealing lip means for bearing against the surface of the face of a mask user, a respiratory gas conduit means for feeding respiratory gas to a mask internal space which is defined by the arch body and which is in communication with the nose and/or mouth opening of the user of the mask, and an application structure for application of the sealing lip jointly with the arch body, wherein the application structure has a carrier portion on which a respiratory gas conduit member is mounted.

In that way it is advantageously possible to provide a breathing mask arrangement which is of a robust structure and which can be cleaned in an advantageous manner and which is distinguished by a high level of sealing integrity.

In accordance with a particularly preferred embodiment of the invention the respiratory gas conduit member is in the form of a tube connection. Such a tube connection is preferably made from dishwasher resistant plastic material so that the respiratory gas conduit member can be cleaned at comparatively high temperatures and in the process sterilised. The tube connection is preferably of such a configuration that its inside diameter is in the region of 12 to 34 mm. The tube connection can be of a substantially circular or preferably polygonal cross-section. The tube connection can be in the form of a conduit bend which provides for a slight change in direction of the flow of respiratory gas through an angle in the range of from 0 to 45°.

The conduit member which in particular is in the form of a tube connection is preferably releasably mountable to the carrier portion. A latching device is preferably provided for coupling the respiratory gas conduit member to the carrier portion. In accordance with a particular aspect of the present invention that latching device is advantageously in the form of a bayonet or rotational latching device.

The application structure of the breathing mask arrangement advantageously includes a frame portion which can be releasably coupled to the sealing lip means and/or to the arch body. Preferably the frame portion is designed in such a way that it embraces the arch body in a ring or loop configuration. The carrier portion is advantageously Made from plastic material and is provided with holding members, by way of which the carrier portion can be coupled for example to a lower web band arrangement of a headband. Advantageously those holding members are in the form of holding loops or clips, through which an end portion of the above-mentioned lower web band arrangement can be passed. The holding loops are preferably formed integrally with the carrier portion. The internal peripheral wall of a through opening formed by the holding loops is preferably of a configuration which, in regard to the moulding tool, permits removal of the holding loops from the mould without involving the use of a sliding pusher member.

The carrier portion provided for fixing the respiration gas conduit member is advantageously formed integrally with the frame portion. In that respect the carrier portion is advantageously designed in such a way that it has an insert opening into which the respiratory gas conduit member can be releasably inserted. The carrier portion is preferably arranged in such a way that it extends substantially perpendicularly to a frame surface defined by the frame portion.

In the region of the insert opening, the carrier portion preferably forms those coupling structures which can be brought into engagement with the respiratory gas conduit member which is in the form of the tube connection.

The arch body preferably comprises a coupling portion, by way of which the arch body can be sealingly connected to the respiratory gas conduit member. Preferably the arch body is produced from an easterner material and fitted with elastic expansion thereof on to a portion of the tube connection, which is passed through the insert opening and which penetrates to the sealing lip means. Preferably, a peripheral bead or ridge is provided on that portion of the tube connection, which extends as far as the sealing lip means, by means of which peripheral bead the arch body and the tube connection are reliably held in the joined condition.

In accordance with a particularly preferred embodiment of the invention the arch body is formed integrally with the sealing lip means that way it is advantageously possible to avoid gaps or joints in the transitional region between the sealing lip means and the arch body. In addition it is advantageously possible for the sealing lip means and the arch body to be inserted in the form of an integral elastomer component into the frame portion.

In accordance with a particularly preferred embodiment, particularly reliable discharge of respiratory gas loaded with $CO_2$ to the ambient atmosphere is attained in that the arch body is provided with openings through which the respiratory gas which is under pressure in the internal region of the arch body can escape to the ambient atmosphere. The openings are preferably such that the cross-section thereof enlarges in the outlet direction. Those outlet openings are preferably arranged in such a way that they are disposed as closely as possible to the region which, in the position of application of the breathing mask arrangement, is adjacent to the nasal openings of a user of the mask.

In accordance with a particular aspect of the present invention the application structure includes a forehead supporting device for supporting the breathing mask arrangement in the forehead region of the user of the mask. The forehead supporting device is advantageously connected by way of a pivot device to the frame portion which embraces the arch body. By virtue of that configuration it is advantageously possible for the position of the forehead supporting device to be adapted to the individual architecture or configuration of the face of the user of the mask. Preferably the pivot device includes an arcuate track guide means by which the forehead supporting device can be variably positioned.

The respiratory gas conduit member which is preferably releasably couplable to the carrier portion advantageously forms a docking port which for example can also form part of a rotary coupling structure. It is possible to provide on the docking port further connecting devices, in particular s small tube connections, by way of which for example a pressure measuring hose can be coupled to the breathing mask arrangement or possibly an additional supply of oxygen can be effected.

The forehead supporting device is preferably made from a thermoplastic material and provided with a forehead cushion means. The forehead cushion means is preferably formed by elastomer elements which are of a pad-like configuration and which can be coupled by way of a plug connecting structure to the receiving portion of the forehead supporting device, said receiving portion preferably being of a loop-like configuration. In that case the forehead supporting device is preferably designed in such a way that the elastomer elements can be fitted to the forehead supporting device at different locations. Preferably the elastomer elements are also of such a configuration that, by virtue of the way in which they are fixed to the loop portion, it is also to achieve different positions of the contact regions of the elastomer elements on the forehead of the user of the mask. The elastomer elements are preferably made from a silicone rubber material and in the region of their contact surface are so shaped that transmission of the contact forces to the surface of the forehead of the user of the mask takes place under a physiologically well compatible surface pressure. That can be achieved in particular by the elastomer elements being provided, on a rear side remote from their contact side, with an eccentrically arranged support foot which permits a tilting movement of the contact portion which bears against the user of the mask.

Preferably, also provided on the loop portion are coupling portions which permit coupling of the forehead supporting device to an upper n forehead hand arrangement of a headband. Those coupling portions can be in the form of a hand strip. It is also possible for the forehead supporting device to be fixed for example by way of a hook-and-loop fastener to a preferably cushioned forehead hand arrangement.

In accordance with a further aspect of the invention, another object of the invention is to prevent the occurrence of any pressure points in the forehead region in connection with the use of breathing masks.

In accordance with the invention that object is attained by a forehead support device for a breathing mask comprising a contact dement which is provided in the application position for bearing against the forehead region of a user of the mask, wherein there is provided a holding device for holding the contact element movably.

By virtue thereof it is advantageously possible to ensure that a breathing mask arrangement is supported in the forehead region of a patient under a markedly reduced surface pressure against the tissue of the patient. The mobility of the contact element, which is provided in accordance with the invention, means that it can automatically adapt to the individual curvature of the forehead region of the user of the mask. In that way it is further advantageously possible for the contact element to afford a large surface area, whereby it is advantageously possible to achieve a marked reduction in the surface pressure.

An embodiment of the forehead support device, which is preferred in accordance with a particular aspect of the present invention, is afforded in that the holder is in the form of a pivotal holder. That pivotal holder advantageously permits a tilting movement of the contact element about at least one axis substantially parallel to the usual contact orientation. That pivotal holder can preferably be formed by a pivot or hinge device which in accordance with a particularly preferred embodiment includes a ball joint. As an alternative thereto or also in combination with that configuration, it is possible for the pivot device to be formed by an elastomer structure. The range of movement of the holder of the contact element is preferably in the range of 10-30°. It is possible to take sufficient account of all possible forehead architectures within that angular range.

In accordance with a particular aspect of the present invention the contact element is formed from an elastomer material, for example a fully transparent or coloured silicone rubber material. Particularly in this embodiment the contact element is preferably of a pad-like or plate-like configuration. In that case, the contact element is preferably concavely inwardly curved in such a way that a defined distribution in terms of surface pressure is afforded when the contact element is applied to the surface of the forehead, in accordance with a particularly preferred embodiment of the invention that surface pressure is so selected that, within a predetermined spacing from the edge of the contact element, there is a substantially uniform surface pressure, with the surface pressure gradually decreasing outwardly in the edge region of the contact element.

In accordance with a particularly preferred embodiment of the invention the forehead support device includes a plurality of and preferably two mutually adjacently arranged contact elements. The contact elements are preferably arranged in such a way that in the application position of a breathing mask arrangement, they are positioned above the left and right eyebrows of the user of the mask. The two contact elements are preferably is connected together by way of a flexible bridge or strap device. In that way, it is possible on the one hand to achieve a greater increase in the contact area while at the same time the possibility of the contact elements twisting relative to each other can he limited in a defined manner. Particularly in this embodiment the two contact elements are preferably formed integrally with each other. The configuration of the contact elements in a plan view is not limited to substantially circular external contours. For example it is also possible to adopt elliptical or other polygonal external contours.

The pivot device for pivotally movably mounting the respective contact element is preferably also formed integrally with the contact element. A defined pivot character can be achieved by virtue of suitable geometrical configuration of the pivot device.

The pivot device is preferably arranged in such a way that it is disposed on or et least near the line of action of a force which extends through a centre point in terms of surface pressure of the respective contact element. That still further promotes rendering the distribution of surface pressure uniform.

The contact elements are preferably profiled in such a way that the contact element is prevented from being applied by suction to the surface of the forehead of the patient. Suction of the forehead support device on the surface of the forehead of the patient can further also be obviated by the contact element being provided with through bores or also with passages, through which air can pass into an intermediate region between the contact element and the forehead of the user of the mask.

The ball joint structures advantageously provide for good adaptability to the horizontal and vertical configuration of the forehead of the user of the mask. The pivot device—it particular the ball joint means—can also be designed to be lockable. The pivot device can also preferably be tiltable in a particularly advantageous manner about given axes—in particular about a horizontal axis. The curvature of the contact element can be so selected that different radii of curvature are afforded in the horizontal and vertical directions. The radii of curvature are preferably smaller than the usual radii of curvature of a forehead.

As an alternative to ball joint structures it is also possible to adopt cardanic suspension means, for example by means of a pivot pin. The angle of pivotal movement of the pivot device is preferably limited to a predetermined abutment angle. The material properties of the contact element are preferably so selected that it has a substantially anti-bacterial action and possibly acts to promote the healing of wounds.

Advantageously, a cushion means, in particular a gel body cushion means, or also an air or liquid cushion means, can be provided in the region of the contact surface. In that case, by varying the amount of liquid, air or gel used, it is advantageously possible to adjust the position of the breathing mask relative to the user.

Advantageously the mounting position of the contact element is adjustably variable. As an alternative thereto—or also in combination with this feature—it is also possible to provide a plurality of coupling options so that it is possible to achieve varying spacings on the forehead, by suitable selective coupling. It is possible to implement coarse adjustment by for example two, preferably three or also more coupling options, and to implement preferably stepless fine adjustment within a limited fine adjustment range. It is possible to permit a plurality of permutation options, in which case the individual coupling permutations result in respectively different settings in terms of the spacing relative to the forehead. It is also possible to provide clamping structures, by means of which stepless adjustment of the spacing relative to the forehead is possible. The coupling means can be so designed that a defined adhesive location is achieved, so that a setting which is individually steplessly adapted is durably maintained by adhesive means.

In accordance with a particularly preferred embodiment of the invention a particularly high level of wearing comfort is achieved in that the surface portions of the contact element, which come into contact with the surface of the skin of the user of the mask, have a surface which is velvety matt. In accordance with a particularly preferred embodiment of the invention, at least in the region of the contact surface of the contact element, there is provided a surface structure for affording a self-cleaning effect. Such a surface structure may have for example lotus leaf surface structures. The contact element may also be provided with a gel body, at least in the region of the contact surface.

BRIEF DESCRIPTION OF THE DRAWINGS

Further details and features of the invention will be apparent from the description hereinafter with reference to the drawings in which.

DETAILED DESCRIPTION OF THE DRAWINGS

Figure 1:
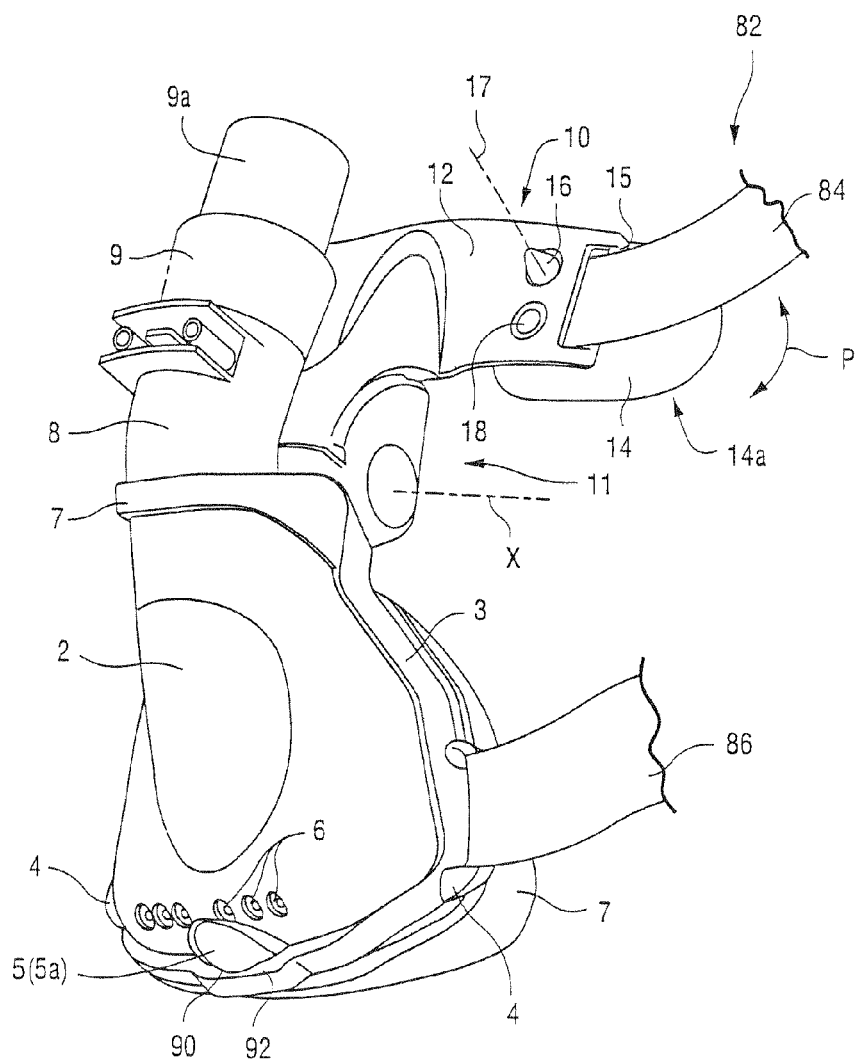
FIG. 1 shows a perspective view of a breathing mask arrangement according to the invention.

The breathing mask arrangement shown in FIG. 1 includes a sealing lip means 1 made from an elastomer material, in particular silicone rubber, and an arch body 2. The sealing lip means 1 is designed in such a way that it lines a receiving opening provided to receive the nose region of a user of the mask, and in that situation preferably passes across the bridge of the nose and the upper lip region of the user of the mask. In this case the sealing lip means 1 is of a substantially saddle-shaped silhouette. In this embodiment, the sealing lip means 1 and the arch body 2 are made in one piece from an elastomer material and are accommodated in a frame portion 3.

The frame portion 3 is made from a plastic material and has holding clips or loops 4 which are produced integrally therewith. In the application position of the breathing mask arrangement the holding loops 4 are disposed at cheek level or at the level of the sides of the nose of the user of the mask and permit coupling of a lower web band arrangement. For reliably coupling the arch body 2 to the frame portion 3, there is a retaining structure 5, by way of which the arch body 2 can be fixed to the frame portion 3 in the joining position by latching engagement therein. The retaining structure 5 includes a retaining nose 5a which engages over a top side of the frame portion 3.

Provided on the arch body 2 are a plurality of outlet openings 6 for the discharge of used respiratory as to the ambient atmosphere.

The breathing mask arrangement further includes a carrier portion 7 which in this embodiment is formed integrally with the frame portion 3.

A respiratory gas conduit member which here is in the form of a docking port 8 is releasably fixed to the carrier portion 7. The docking port 8 includes an annular flange (not visible here) on to which a hose connecting sleeve 9 is rotatably movably fitted. The hose connecting sleeve 9 includes a hose connecting portion 9a on to which an end portion of a respiratory gas hose can be fitted.

The breathing mask arrangement according to the invention further includes a forehead supporting device 10 which is coupled movably to the frame portion 3 by way of an adjusting device 11.

The adjusting device 11 is of such a configuration that it permits a pivotal movement of the forehead supporting device 10 with respect to the frame portion 3 about the pivot axis X which is shown here. The adjusting device 11 includes a fixing mechanism, by which the forehead supporting device 10 and the frame portion 3 can be fixed in the selected relative position.

The forehead supporting device 10 includes a loop portion 12 to which forehead cushion elements 14 can be mounted. Provided on the loop portion 12, similarly to the frame portion 3, are holding loops or clips 15, for coupling the loop portion 12 to an upper web band arrangement of a headband provided for fixing the breathing mask arrangement in place.

The forehead cushion elements 14 are made from an elastomer material and, on their underside 14a which in the application position faces towards the user of the mask, form a contact surface involving a predetermined distribution in terms of surface pressure. The forehead cushion elements 14 are each coupled to the loop portion 12 by way of a respective push-in foot 16. The push-in foot 16 is provided eccentrically on the respective forehead cushion element 14 in such a way that pivoting the forehead cushion elements 14 about the axis 17 of the push-in foot, as indicated by the arrow P, makes it possible to achieve different contact positions for the underside 14a of the forehead cushion elements 14 on the surface of the forehead of the user of the mask. Different contact positions can be achieved by virtue of selection of the pivotal position of the forehead cushion element 14 and by virtue of selection of the receiving opening 18 provided to receive the push-in foot 16. In the embodiment illustrated here, two mutually spaced receiving openings 18 are provided in the loop portion 12, for each of the left and the right forehead cushion elements 14.

Figure 2:
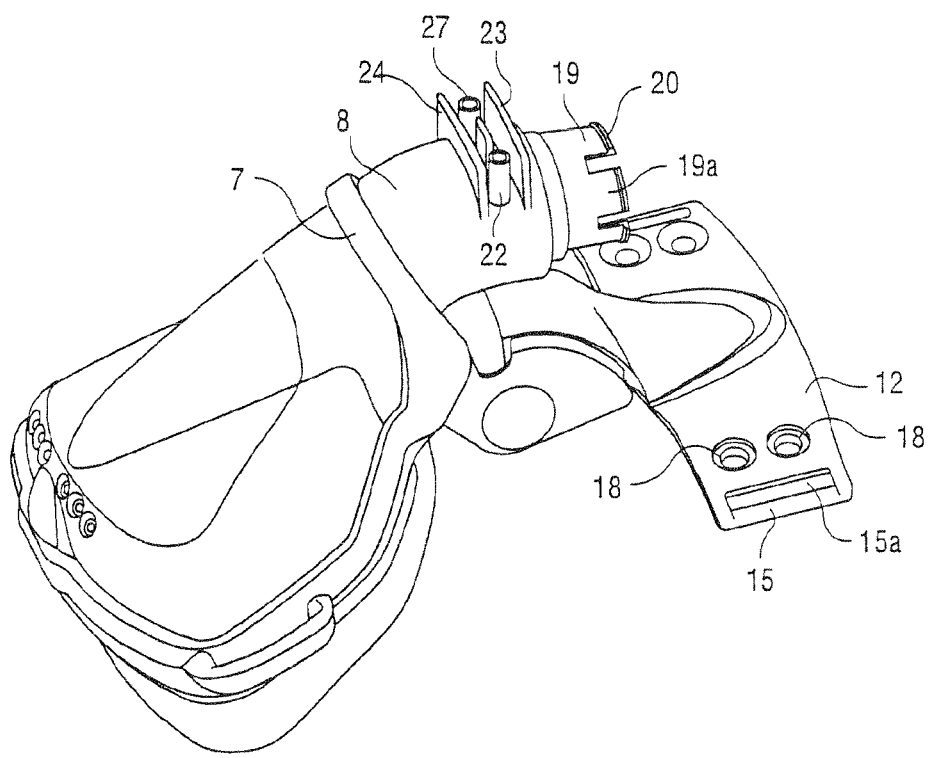
FIG. 2 shows a further perspective view of the breathing mask arrangement according to the invention without hose connecting sleeve.

The forehead cushion elements 14 can be removed from the loop portion 12 by pulling the push-in feet 16 out of the receiving openings as is shown in FIG. 2. In this embodiment, the centre lines of the receiving openings 18 are spaced from each other by approximately 10 mm. The eccentricity of the push-in foot 16 on the respective forehead cushion element 14 (see in that respect FIG. 1) is also about 10 mm. As a result of the eccentric arrangement of the push-in foot 16 and the spaced arrangement of the receiving opening 18, heightwise variability of the forehead cushion elements in a range of about 30 mm is achieved substantially perpendicularly to a line joining the eyebrows of the user of the mask. A variation in the contact position over a range of 20 mm is also possible in a lateral direction, that is to say in the direction of the above mentioned line which joins the eyebrows. The holding loop 15 provided for coupling an upper web band arrangement is arranged in the proximity of the receiving openings 18 in such a way that the through opening 15a defined by the holding loop is covered over towards the user of the mask by the forehead cushion element 14.

In the view shown in FIG. 2 the hose connecting sleeve 9 shown in FIG. 1 has been removed from the docking port 8. It is possible in this view to see an annular flange 19 which is formed integrally with the docking port 8 and which has a plurality of tongue elements 19a which are elastically deflectable towards the centre of the through passage formed by the docking port 8. Provided on the tongue elements 19a is a retaining bead or ridge 20 which can be brought into engagement with an internal peripheral groove provided in complementary relationship on the hose connecting sleeve 9. The geometry of the retaining bead 20, the internal peripheral groove in the rotational sleeve 9 and the elasticity of the tongue elements 19a are so matched that the hose connecting sleeve 9 can be withdrawn from the annular flange 19 without involving the use of a tool, when a oven pulling force is exceeded. The annular flange 19 and the hose connecting sleeve 9 are also designed to fit in such a way that the hose connecting sleeve 9 is easily rotatably carried on the annular flange 19.

In this embodiment the docking port 8 is provided with hose connecting, portions 21, 22, on to which a plug or hose element can be fitted. The hose connecting portions 21, 22 each form a respective through passage which opens into the respiratory gas passage formed in the docking port 8. When not in use, the hose connecting portions 21, 22 can be closed by a plug or cap element (not shown) which is preferably fitted in frictionally locking relationship on the hose connecting portions 21, 22. In this embodiment the hose connecting portions 21, 22 are arranged recessed in a groove which is delimited by two upstanding groove walls 23, 24. The docking port 8 is coupled to the carrier portion 7 by way of a plug-in connecting structure.

Figure 3:
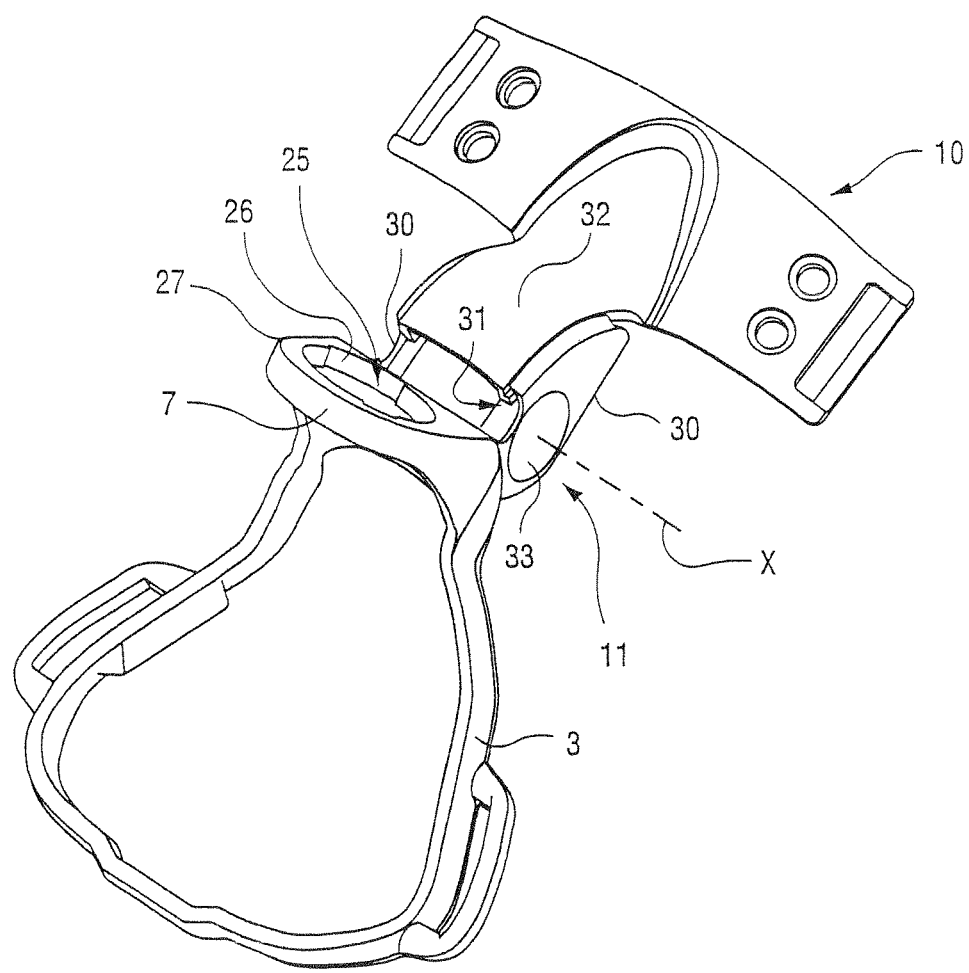
FIG. 3 shows a perspective view of the application structure of the previously illustrated breathing mask arrangement.

The retaining connecting structure for coupling the docking port 8 to the carrier portion 7, as can be seen from the view in FIG. 3, in this embodiment, is in the form of a rotary latching or bayonet connecting structure 25. The bayonet connecting structure 25 includes two mutually diametrally opposite retaining bridges 27 which are separated from each other by insertion recesses 26. In the locking position the retaining bridges 27 come into engagement with two retaining projections which are provided on a push-in flange portion 28 (FIG. 4) of the docking port.

The carrier portion 7 is formed integrally with the frame portion 3 and in that respect forms the insert opening which is provided to receive the insert connection 26 and which is partially lined by the retaining bridges 27. Provided in the transitional region between the carrier portion 7 and the frame portion 3 are two guide flanks 30 which are also provided integrally with the frame portion 3 and form part of the adjusting means 11. The guide flanks 30 form an arcuate guide means 31 in which a coupling portion 32 of the forehead supporting device 10 is displaceably guided. The arcuate guide means 31 and the region of the coupling portion 32, which is guided therein, are such that the forehead supporting device 10 and the frame portion 3 are movable relative to each other about the pivot axis X already shown in FIG. 1. Provided at the guide flanks 30 is an actuating zone 33, for applying the release force for moving the adjusting means 11 into a release position. The release force can be applied to the actuating zone in particular when gripping around the docking port 8 with the thumb and the index finger and applying the corresponding fingertips. As an alternative to the arcuate guide means 31 provided here, it is also possible for the adjusting means 11 to be of such a configuration that relative movement is made possible between the forehead supporting device 10 and the frame portion 3 along a path of movement which differs from an arcuate path. It is also possible to mount to the forehead supporting device 10 forehead cushion devices which in their structure differ from the forehead cushion elements 14 shown in FIG. 1.

Figure 4:
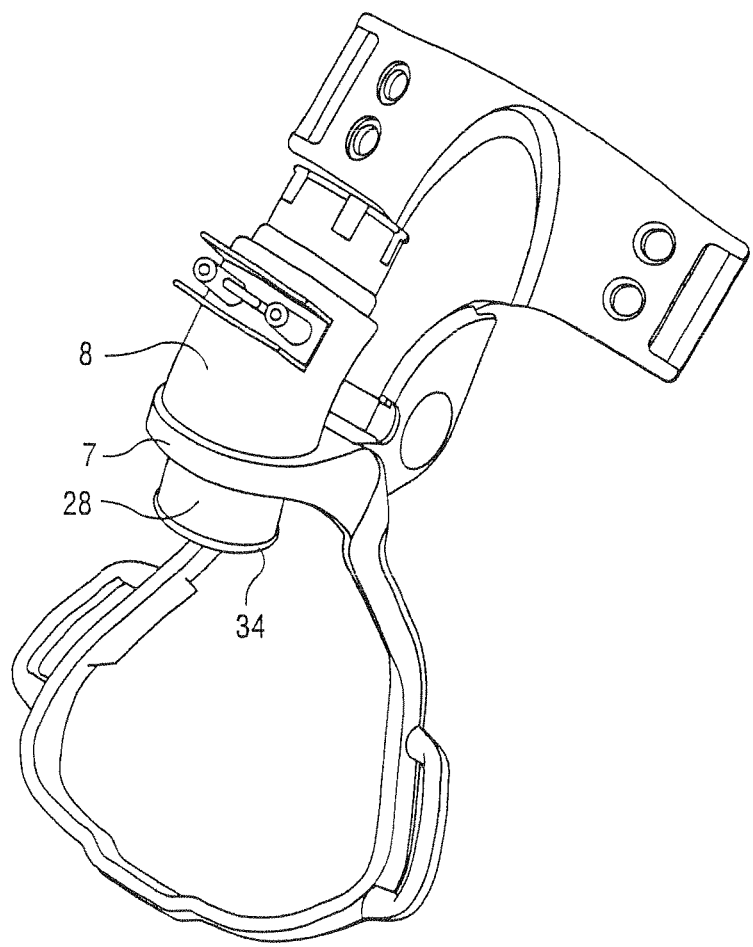
FIG. 4 shows a perspective view of the application structure with a docking port connected thereto.

FIG. 4 shows the application structure of the breathing mask arrangement according to the invention, in an assembly condition in which the docking port 8 according to the invention is inserted into the insert opening formed in the carrier portion 7 and correctly fixed in position by way of the bayonet closure device provided in the region of the insert opening. In this embodiment, the docking port 8 forms a conduit member which is in the nature of a pipe bend and by which the flow of respiratory gas flowing by way of the hose connecting sleeve 9 (FIG. 1) is diverted through an angle of about 30° towards the tip of the nose of the user of the mask. Feeding the respiratory gas in that way to the internal space in the mask, which is defined by the arch body 2 (FIG. 1), provides that the gas advantageously flows over the bridge of the nose of the user of the mask.

The modular structure of the breathing mask arrangement according to the invention makes it possible to implement a configuration of the breathing mask arrangement, which takes better account of the respective situation of use. The docking port 8 which is fitted into the carrier portion 7 has an insert connecting portion 28 which projects beyond the carrier portion 7 towards the frame portion 3. An insert opening portion of the arch body 2 can be fitted on to the insert connecting portion 28, with slight elastic expansion. Provided on the insert connecting portion 28 is a peripheral bead 34, by which the arch body 2 and the insert connecting portion 28 are held in a defined joint position. That peripheral bead 34 can come into engagement with an internal peripheral groove correspondingly provided in the arch body 2, or it can fit on an internal surface of the arch body 2. The carrier portion 7 and the docking port 8 are of such a configuration that the docking port 8 forms a respiratory gas conduit portion which bridges over the region of the bridge of the nose. That ensures that the field of vision is only slightly impaired.

Figure 5:
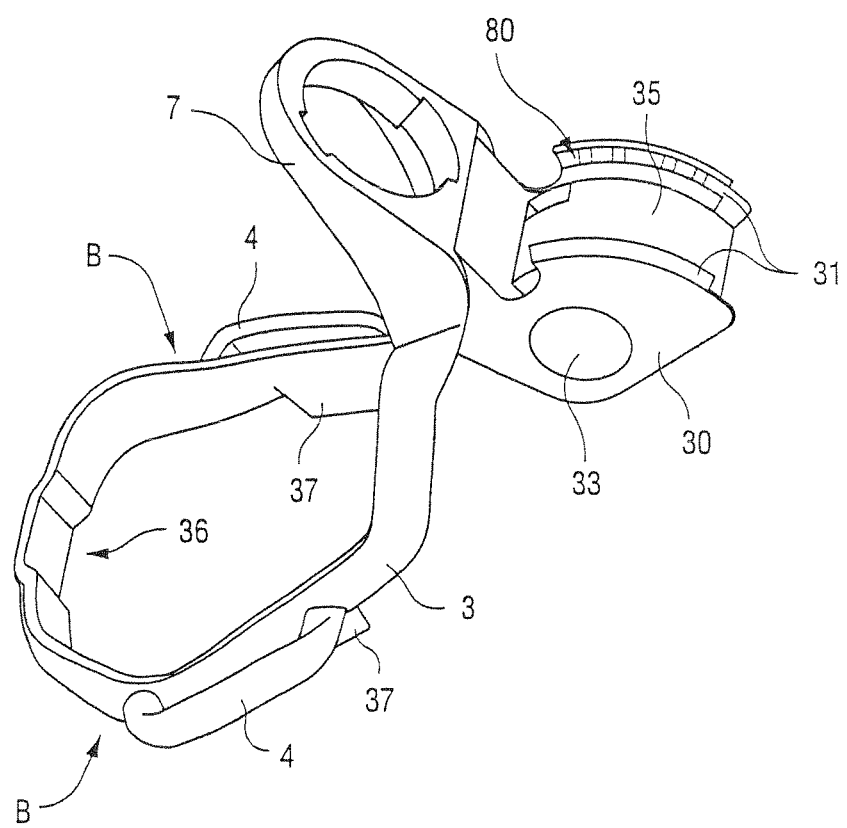
FIG. 5 shows a perspective view of an integral member formed from a carrier portion and a frame portion.

FIG. 5 shows a further perspective view of the integral member forming the frame portion 3. The guide flanks 30 which are made in one piece with the frame portion 3 are of such a configuration that application of a release force to the actuating zones 33 urges the guide flanks 30 away from each other in the region of the arcuate guide means 31. In the present embodiment, for that purpose, a lever/tilting effect is produced by an arcuate leg 35. The return movement of the guide flanks 30 in the region of the arcuate guide means 31 takes place as a consequence of the elasticity of the material involved. The fixing effect can be achieved by virtue of frictionally locking damping of the contact zones of the coupling portion 32, which are guided between the guide flanks 30. As an alternative thereto or in combination therewith, it is also possible to achieve the fixing effect by coupling in positively locking engagement, for example by the adoption of a fine tooth arrangement.

Preferably, there is provided an abutment device which limits the maximum range of pivotal movement of the forehead supporting device 10 with respect to the frame portion 3. It is possible for that abutment device to be so designed that, for example by increasing the actuating forces applied to the actuating zone 33, the abutment device is moved into a condition in which the forehead supporting device 10 can be separated from the pivot structure connected to the frame portion 3.

The view illustrated in FIG. 5 also shows an outwardly recessed region 36 in the frame portion 3, which improves positioning and fixing of the arch body 2 in the frame portion 3. Positioning of the arch body 2 in the frame portion 3 is further promoted by two fixing plates 37 which are provided in: the region of the holding loops 4 at the underside of the frame portion 3 and which engage into clamping pocket portions provided in the transitional region of the sealing lip means 1 in the arch body 2. The frame portion 3 is of a substantially saddle-shaped silhouette and attains its maximum width in a region of the frame portion 3, which in the application position of the breathing mask arrangement is approximately at the height of the sides of the nose of the user of the mask. The holding loops 4 extend upwardly from that zone B of maximum width to the region of the eyes of the user of the mask. The inward edges of the through openings which are bordered by the holding loops 4 are of a rounded configuration in order to prevent the band portions which are passed through those openings from possibly being chafed through. This view again shows the latching device adapted for fixing the docking port in the carrier portion 7.

Figure 6:
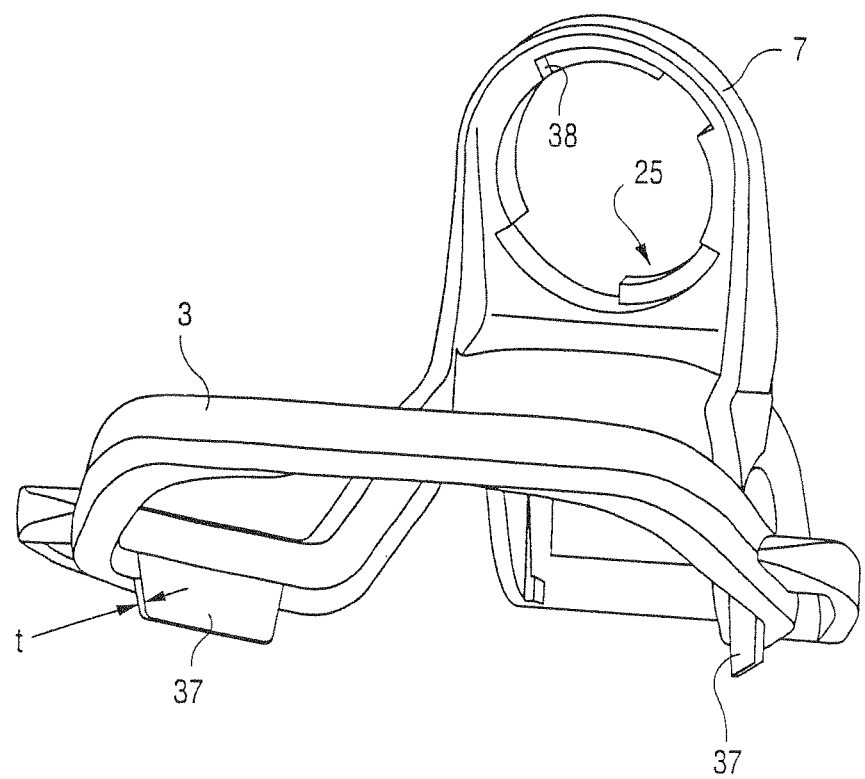
FIG. 6 shows a further perspective view of the integral member shown in FIG. 5 to describe the latching device provided for coupling the docking port.

FIG. 6 shows the fixing plates 37 which are provided at the underside of the frame portion 3, from another perspective. The fixing plates 37 are of a thickness t as measured transversely to the joining direction in the range of from 0.8 to 3 mm. The fixing plates are of a tapered configuration in the joining direction. The fixing plates 37 and in particular also the internal peripheral region of the frame portion 3, which region bears against the arch body 2, can be provided with a profiling which still further assists with coupling of the arch body. Preferably, fine profile grooves extending in the peripheral direction of the frame portion 3 are provided on the frame portion 3 and on the portion of the arch body 2, which bears thereagainst.

The bayonet connecting structure 25 on the carrier portion 7 includes an end abutment 38 for defining the end position of the docking port 8 in the coupling position. In this embodiment the bayonet connecting structure 25 is designed in such a way that the maximum fixing force is achieved in the end position defined by the end abutment 38.

Figure 7:
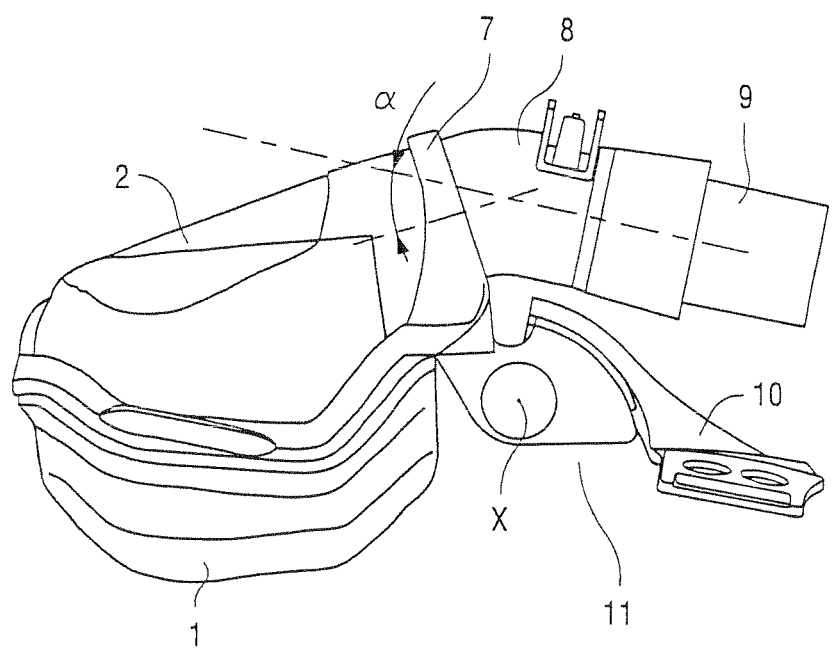
FIG. 7 shows a side view of the breathing mask arrangement according to the invention.
Figure 11:
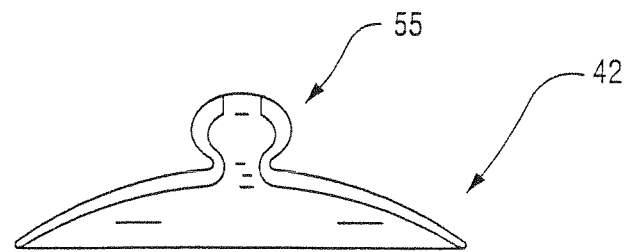
FIG. 11 shows a further embodiment of a contact element with a concavely curved contact surface and a part-spherical portion for pivotably mounting the contact element.

FIG. 7 shows the breathing mask arrangement according to the invention—with the exception of the forehead cushion elements 14 (FIG. 11 in the completely assembled condition, from the direction of the pivot axis X. As can be seen in that view the docking port 8 which n accordance with the invention can be releasably inserted into the carrier portion 7 forms a coupling element for coupling the elastomer arch body 2 to a rotatably supported hose connecting sleeve 9, by which the feed flow of respiratory gas is deflected through an angle α which in this embodiment is 32°.

The docking port 8 can be selected from a set which includes a plurality of docking ports 8 and forms an interface member by which the arch body 2 can be coupled to different hose systems. Compatibility with different respiratory gas conduit systems can also be ensured by way of the hose connecting sleeve 9 which is fitted on to the docking port 8. It is possible to provide a plurality of sealing lip means which are respectively adapted to given types of faces and to achieve a configuration which is appropriate to the requirements involved, for the breathing mask arrangement according to the invention, in that an elastomer element which takes particularly good account of the individual facial architecture of the user of the mask and which comprises the sealing lip means 1 and the arch body 2 is integrated into the mask arrangement according to the invention. It is also possible to provide a plurality of variants of the forehead support device, which however are compatible with the adjusting means 11, and to fit the mask arrangement according to the invention with a variant of the forehead supporting device 10 which takes particularly good account of the individual facial architecture. As an alternative to the forehead cushion elements shown in FIG. 1, the forehead supporting device 10 may also be fitted with other kinds of forehead cushion devices for cushioned contact against the forehead of the user of the mask. It is possible to integrate cushion devices of that kind, for example into an upper forehead band arrangement, and to fit the forehead supporting device on to that cushioned forehead band arrangement, for example by way of a hook-and-loop fastener structure.

Figure 8:
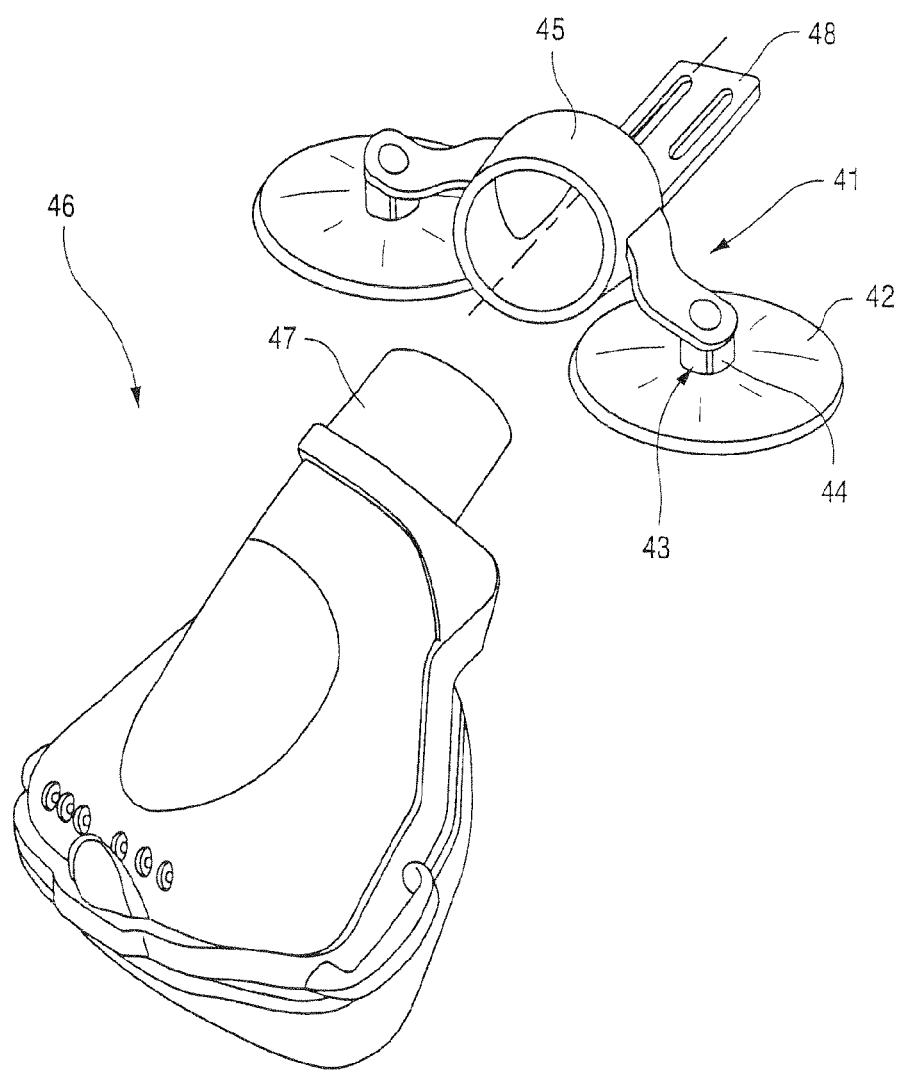
FIG. 8 shows a simplified perspective view of a forehead support device with two pivotably mounted pad-like contact elements and by way of indication a breathing mask.

The invention is not limited to the preceding embodiment. By way of example, it is also possible to fit into the frame portion 3 which is designed in accordance with the invention, an arch body 2 which is not made from an elastomer material, The forehead support device shown in FIG. 8 has a holding device 41 for pivotably holding a contact element 42. The holding device 41 for that purpose includes a pivotable holder 43 which here has a plurality of fixing elements 44 which form part of a ball joint arrangement.

In the embodiment illustrated here, the contact element 42 is of a plate-like configuration and is formed from an elastomer material, here fully transparent silicone rubber. The contact element 42 is mounted tiltably about at least two axes in space by way of the fixing elements 44. In order to ensure as easy mobility as possible of the contact element 42, provided between the fixing elements 44 and a fixing shank portion (not visible) of the contact element 42 is a ring body which has a spherical external surface (details in relation thereto will be described more fully with reference to FIG. 9).

The holding device 41 further includes a coupling portion 45 for coupling the holding device 41 to a breathing mask 46.

In the embodiment illustrated here the coupling portion, 55 is in the form of a ringlike element which can be fitted directly on to a connecting portion 47 of the breathing mask 46, the connecting portion 47 being of a correspondingly complementary configuration. In the embodiment illustrated here the holding device 41 is provided with a fixing portion 48 and can be connected by way thereof to a headband.

Figure 9:
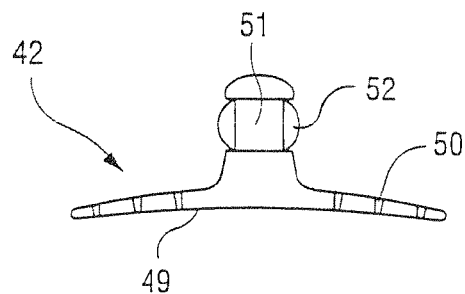
FIG. 9 shows a simplified sectional view to illustrate a preferred embodiment of a pivotably mounted contact element.

FIG. 9 shows a preferred embodiment of the contact element 42. The contact element 42 is formed from an elastomer material and has a contact surface 49 which is slightly concavely curved. The contact element 42 is provided with a plurality of fine through bores 50 through which pressure equalisation with the ambient atmosphere can be achieved in respect of the intermediate space possibly defined between the contact element 42 and the forehead of the patient. That advantageously prevents the contact element 42 from being sucked against the forehead region of the patient.

In the embodiment illustrated here the contact element 42 has a shank portion 51. Provided on the shank portion 51 is a ring element 52 which forms a spherical external surface. In conjunction with that ring element 52, this arrangement affords a comparatively easily movable ball joint device. As an alternative thereto it is also possible to forego the ring element and to provide the corresponding spherical portion directly on the shank portion 51 of the contact element 42.

Figure 10:
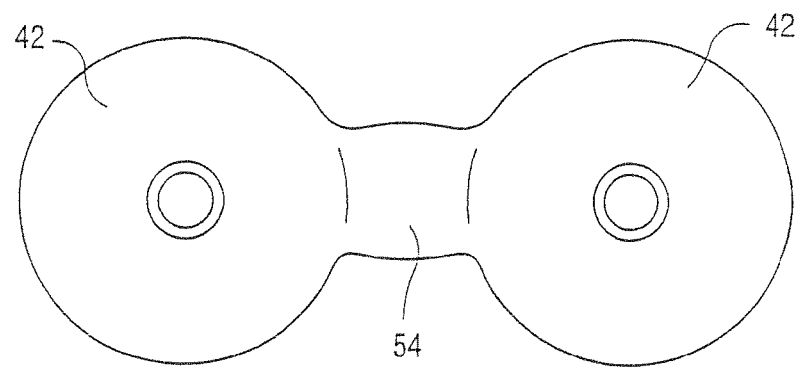
FIG. 10 shows a plan view of two contact elements which are formed integrally with each other, each of which is individually provided with a pivotal mounting means.

The embodiment of the invention shown in FIG. 10 has two contact elements 42 which are connected together by way of an integral central bridge or strap 54. The central strap 54 is so designed that it still permits pivotal movement and tilting movement of the two contact elements 42 relative to each other over a sufficient angular range. The spacing of the centres of the two contact elements 42 from each other preferably approximately corresponds to the distance between the eyes of the user of the mask.

FIG. 11 shows a further embodiment of a contact element 42, in which case tiltability of the portion of the contact element, which forms the contact surface, is achieved by way of an elastomer structure 55 which here is formed integrally with the contact element 52. In the embodiment illustrated here the elastomer structure includes a substantially spherical internal space which can be fitted on to a spherical trunnion portion, with temporary elastic expansion. In the embodiment illustrated here the contact element also has a concavely curved base body which is flattened when the contact element is appropriately fitted in position.

Figure 12:
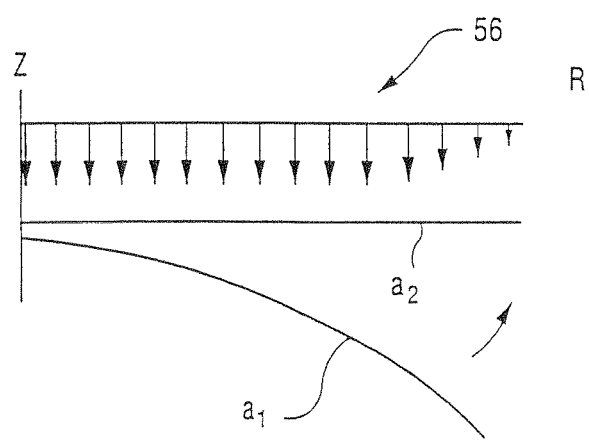
FIG. 12 shows a sketch to describe a preferred distribution of surface pressure from a central region of the contact element in its variation from a centre region of the contact element towards the edge region thereof.

The curvature of the base body of the contact element is preferably so selected that a defined distribution in terms of contact pressure is afforded when it is applied to a flat surface. That distribution in respect of contact pressure is shown by way of example in FIG. 12. The lower curved line a1 in this case symboiises the contact surface of the contact element in its initial position. The line a2 which is shown her as being straight symbolises the contact surface of the contact element 42, when appropriately deformed in the application position. The distribution in terms of surface pressure, which is indicated here in simplified form by an assembly of arrows 56, occurs in the context of deformation of the contact surface of the contact element. The distribution in terms of surface pressure is selected here in such a way that, starting from the centre Z IC towards the edge region, there is initially a substantially uniform distribution in terms of surface pressure, with the surface pressure gradually decreasing in the region of r/5 towards the edge R.

The invention is not limited to the embodiments described hereinbefore. For example, it is also possible, in a departure from the plate-shaped configuration selected here, for the forehead contact elements to be of a rectangular or polygonal configuration.

The invention claimed is:

1. A breathing mask arrangement, comprising:
   a frame portion;
   a sealing lip provided to the frame portion and adapted to form a seal with a user's face;
   a forehead support provided to the frame portion; and
   a forehead cushion removably secured to the forehead support,
   the forehead cushion including a contact portion having a contact surface adapted to contact a user's forehead and a connecting structure structured to couple the forehead cushion to the forehead support and allow pivoting and/or tilting movement of the contact portion relative to the forehead support, the connecting structure including a support foot adapted to be received within a respective opening provided in the forehead support.

2. A breathing mask arrangement according to claim 1, wherein the forehead support includes arm elements adapted to support the forehead cushion, each arm element including an end portion that provides an opening through which a portion of an upper headband arrangement is structured to pass.

3. A breathing mask arrangement according to claim 2, wherein the forehead support is T-shaped.

4. A breathing mask arrangement according to claim 3, wherein the forehead cushion is formed of an elastomeric material.

5. A breathing mask arrangement according to claim 4, wherein the contact portion includes a pad like configuration.

6. A breathing mask arrangement according to claim 5, wherein the contact surface of the contact portion is concavely inwardly curved.

7. A breathing mask arrangement according to claim 6, wherein the forehead cushion includes two forehead cushions.

8. A breathing mask arrangement according to claim 7, wherein the two forehead cushions are connected with each other by a flexible bridge portion.

9. A breathing mask arrangement according to claim 8, wherein the two forehead cushions are formed integrally with one another.

10. A breathing mask arrangement according to claim 9, wherein each forehead cushion includes at least one hole or passage through the contact surface.

11. A breathing mask arrangement according to claim 10, wherein at least a surface portion of the forehead cushion adapted to contact with the skin of the mask user has a velvety matt surface.

12. A breathing mask arrangement, comprising:
a frame portion;
a sealing lip provided to the frame portion and adapted to form a seal with a user's face;
a forehead support provided to the frame portion; and
a forehead cushion removably secured to the forehead support, the forehead cushion including:
a contact portion having a contact side providing a contact surface and a rear side, wherein the contact portion is constructed to pivot and/or tilt relative to the forehead support in use; and
a support foot provided to the rear side of the contact portion.

13. A forehead cushion for a forehead support of a breathing mask arrangement, the forehead cushion comprising:
a cushion element including a contact surface adapted to contact a patient's forehead and provide a distribution of contact force; and
a coupling element provided to the cushion element, the coupling element adapted to couple the cushion element to the forehead support,
wherein the cushion element and the coupling element comprise an integral construction of elastomeric material,
wherein the cushion element is movable with respect to the coupling element to achieve different contact positions on the patient's forehead, and
wherein the forehead cushion includes two forehead cushions connected with each other by an integral flexible bridge portion, the integral flexible bridge portion structured to allow pivotal and tilting movement of the two forehead cushions relative to each other over an angular range.

14. A breathing mask arrangement, comprising:
a frame;
a seal provided to the frame and adapted to receive at least a nose region of a mask user;
a forehead support provided to the frame; and
the forehead cushion according to claim 13 coupled to the forehead support.

15. A breathing mask arrangement according to claim 12, wherein the forehead support includes arm elements adapted to support the forehead cushion, each arm element including an end portion that provides an opening through which a portion of an upper headband arrangement is structured to pass.

16. A breathing mask arrangement according to claim 15, wherein the forehead support is T-shaped.

17. A breathing mask arrangement according to claim 16, wherein the forehead cushion is formed of an elastomeric material.

18. A breathing mask arrangement according to claim 17, wherein the contact portion includes a pad like configuration.

19. A breathing mask arrangement according to claim 18, wherein the contact surface of the contact portion is concavely inwardly curved.

20. A breathing mask arrangement according to claim 19, wherein the forehead cushion includes two forehead cushions.

21. A breathing mask arrangement according to claim 20, wherein the two forehead cushions are connected with each other by a flexible bridge portion.

22. A breathing mask arrangement according to claim 21, wherein the two forehead cushions are formed integrally with one another.

23. A breathing mask arrangement according to claim 22, wherein each forehead cushion includes at least one hole or passage through the contact surface.

24. A breathing mask arrangement according to claim 23, wherein at least a surface portion of the forehead cushion adapted to contact with the skin of the mask user has a velvety matt surface.

25. A forehead cushion according to claim 13, wherein the cushion element and the coupling element are integrally formed as a one-piece structure.

26. A forehead cushion according to claim 13, wherein the coupling element is structured to allow pivoting and/or tilting movement of the cushion element.

27. A forehead cushion according to claim 13, wherein the cushion element includes a pad like configuration.

28. A forehead cushion according to claim 13, wherein the contact surface of the cushion element is concavely inwardly curved.

29. A forehead cushion according to claim 13, wherein the coupling element includes a push-in foot adapted to be received within a respective opening provided in the forehead support.

* * * * *